United States Patent
Motzer et al.

(10) Patent No.: US 9,010,684 B2
(45) Date of Patent: Apr. 21, 2015

(54) AUTOMATED INSPECTION OF SOFT-TOOLED HOLLOW STRUCTURE

(75) Inventors: William P. Motzer, Seattle, WA (US); James C. Kennedy, Renton, WA (US); Michael C. Hutchinson, Kent, WA (US); Martin L. Freet, Federal Way, WA (US); Ronald E. VonWahlde, Puyallup, WA (US); Steven Ray Walton, Wilkeson, WA (US); Jeffry J. Garvey, Burien, WA (US); Scott W. Lea, Renton, WA (US); James J. Troy, Issaquah, WA (US); Daniel James Wright, Mercer Island, WA (US); Hien T. Bui, Kent, WA (US); Michael Joseph Duncan, Lake Tapps, WA (US); Mark L. Little, Auburn, WA (US); William Joseph Tapia, Kapowsin, WA (US); Barry A. Fetzer, Renton, WA (US); Richard C. Krotzer, Enumclaw, WA (US)

(73) Assignee: The Boeing Company, Chicago, IL (US)

( * ) Notice: Subject to any disclaimer, the term of this patent is extended or adjusted under 35 U.S.C. 154(b) by 406 days.

(21) Appl. No.: 13/534,014

(22) Filed: Jun. 27, 2012

(65) Prior Publication Data

US 2014/0005840 A1 Jan. 2, 2014

(51) Int. Cl.
*B64C 1/00* (2006.01)
*B64C 30/00* (2006.01)
(Continued)

(52) U.S. Cl.
CPC ............ *G01N 29/043* (2013.01); *G01N 29/225* (2013.01); *G01N 29/265* (2013.01); *G01N 2291/0231* (2013.01); *G01N 2291/2694* (2013.01)

(58) Field of Classification Search
CPC . G01N 29/043; G01N 29/225; G01N 29/265; G01N 2291/0231; G01N 2291/2694
USPC ................ 244/117 R, 119, 123.14, 131–133; 700/95, 98, 110; 73/618, 621, 634
See application file for complete search history.

(56) References Cited

U.S. PATENT DOCUMENTS 4,138,822 A * 2/1979 Parodi .............................. 33/572
4,741,015 A * 4/1988 Charrier ........................ 378/196
(Continued)

OTHER PUBLICATIONS

Int'l Search Report and Written Opinion, Sep. 10, 2013, Int'l Application No. PCT/US2013/034482 (Int'l counterpart of the instant patent application).
(Continued)

*Primary Examiner* — Ramesh Patel
(74) *Attorney, Agent, or Firm* — Ostrager Chong Flaherty & Broitman P.C.

(57) ABSTRACT

A system and method that allow inspection of hollow structures made of composite material, such as an integrally stiffened wing box of an aircraft. A wing box comprises top and bottom skins connected by a plurality of spaced spars. The system employs a plurality of scanners for inspecting different portions of each spar. The system uses dynamically controlled magnetic coupling to connect an external drive tractor to computer-controlled scanners that carry respective sensors, e.g., linear ultrasonic transducer arrays. A system operator can control the various components by means of a graphical user interface comprising multiple interaction regions that represent the individual scanner motion paths and are associated with respective motion script files.

20 Claims, 22 Drawing Sheets

(51) Int. Cl.
*G01N 29/22* (2006.01)
*G01N 29/265* (2006.01)
*G01N 29/04* (2006.01)

(56) References Cited

U.S. PATENT DOCUMENTS

| | | | |
|---|---|---|---|
| 4,848,159 A | 7/1989 | Kennedy et al. | |
| 6,722,202 B1 | 4/2004 | Kennedy et al. | |
| 6,881,925 B1* | 4/2005 | Sato et al. | 219/121.73 |
| 6,993,971 B2 | 2/2006 | Bossi et al. | |
| 7,231,826 B2 | 6/2007 | Bossi et al. | |
| 7,249,512 B2 | 7/2007 | Kennedy et al. | |
| 7,263,889 B2 | 9/2007 | Kennedy et al. | |
| 7,484,413 B2 | 2/2009 | Georgeson et al. | |
| 7,669,799 B2* | 3/2010 | Elzey et al. | 244/123.12 |
| 7,789,339 B2* | 9/2010 | Sommer | 244/3 |
| 2002/0017140 A1* | 2/2002 | Georgeson et al. | 73/618 |
| 2006/0042391 A1 | 3/2006 | Georgeson et al. | |
| 2006/0162456 A1 | 7/2006 | Kennedy et al. | |
| 2007/0006657 A1 | 1/2007 | Kennedy et al. | |
| 2010/0095775 A1 | 4/2010 | Sarr et al. | |
| 2010/0100085 A1* | 4/2010 | Lewinsky et al. | 606/16 |
| 2010/0116938 A1* | 5/2010 | Kline et al. | 244/131 |
| 2010/0157276 A1* | 6/2010 | Shibazaki | 355/72 |
| 2010/0296070 A1* | 11/2010 | Shibazaki | 355/53 |

OTHER PUBLICATIONS

U.S. Appl. No. 12/966,268, filed Dec. 13, 2010, entitled "Device and Method for Inspecting a Corner Radius."
U.S. Appl. No. 13/313,267, filed Dec. 7, 2011, entitled "Adaptive Magnetic Coupling System."
Troedsson, "Automated ultrasonic field inspection on aircrafts with CFRP composite structure," ATX 2006—Aero NDT Forum, Hamburg, Apr. 5, 2006.
Skramstad, "Improved Methods for Ultrasonic Inspection of Large Carbon Fiber Composite Wing Structure," ATA NDT Forum, Sep. 27, 2011.

* cited by examiner

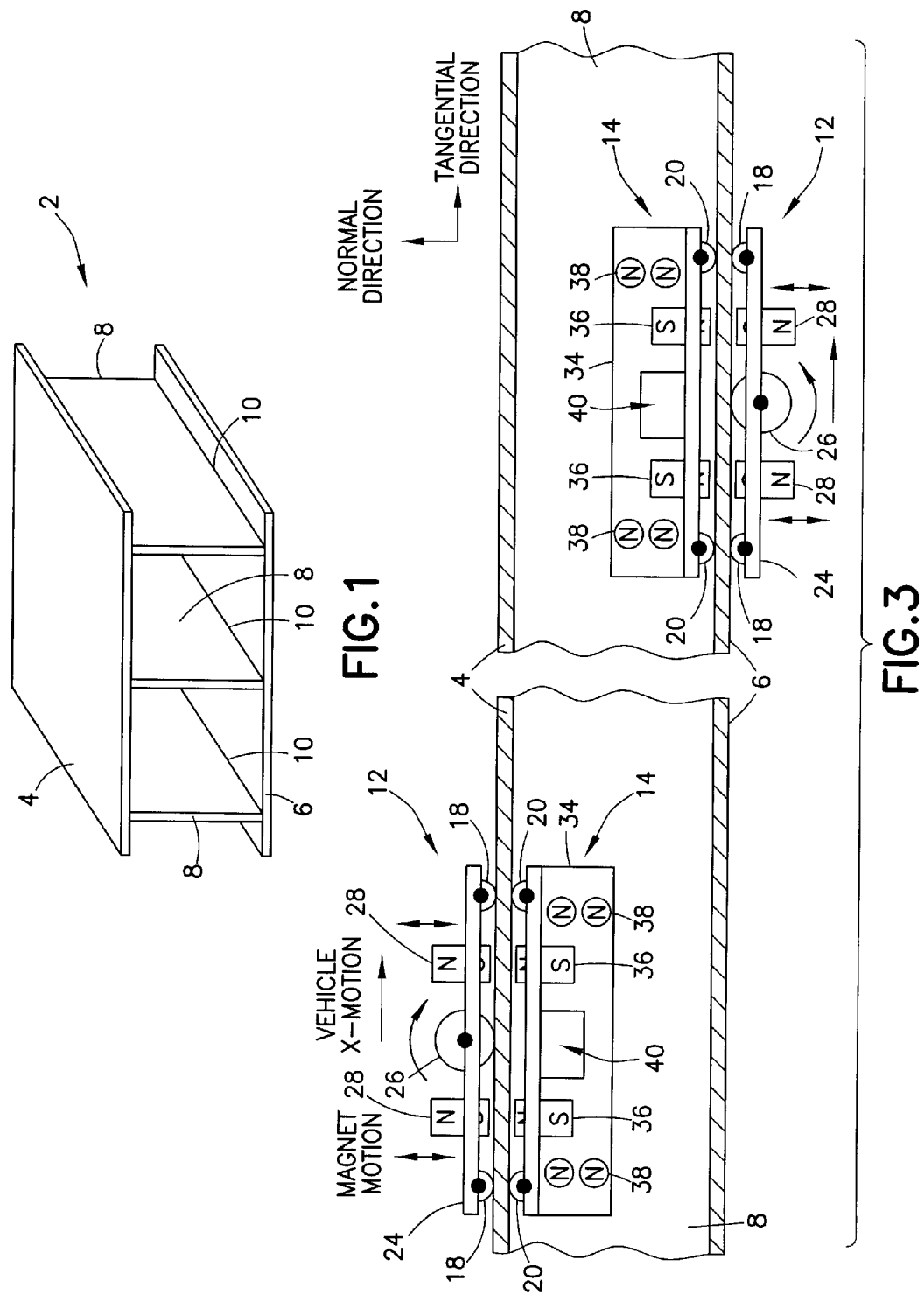

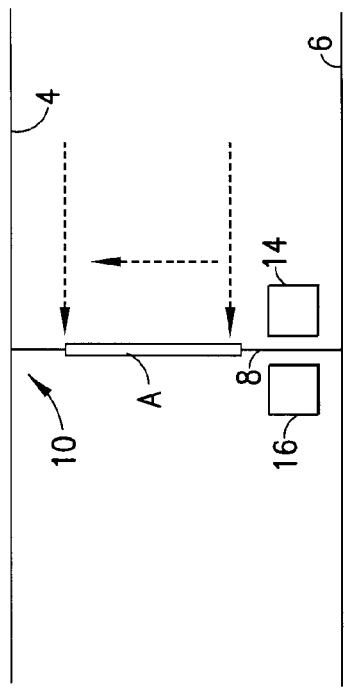
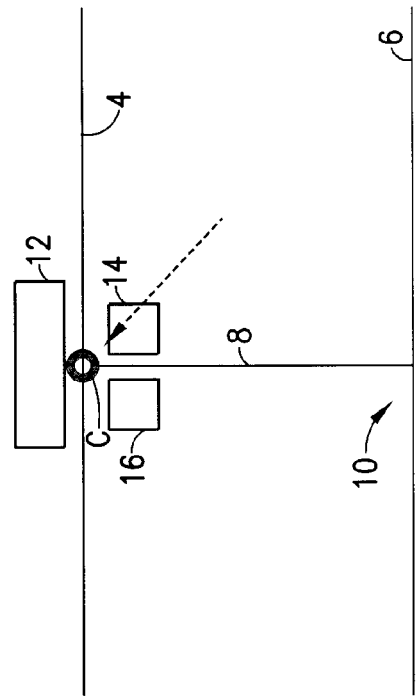
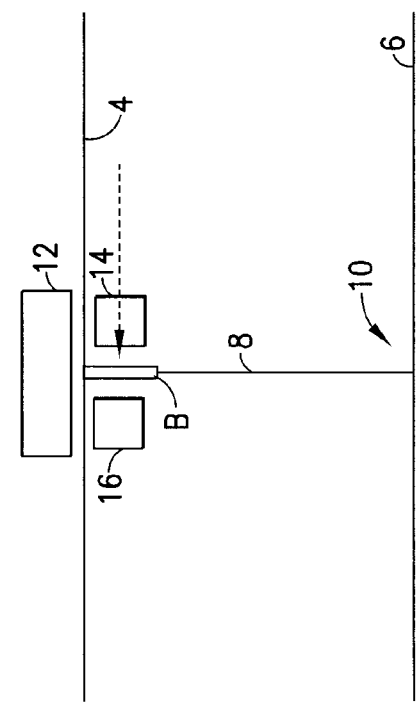

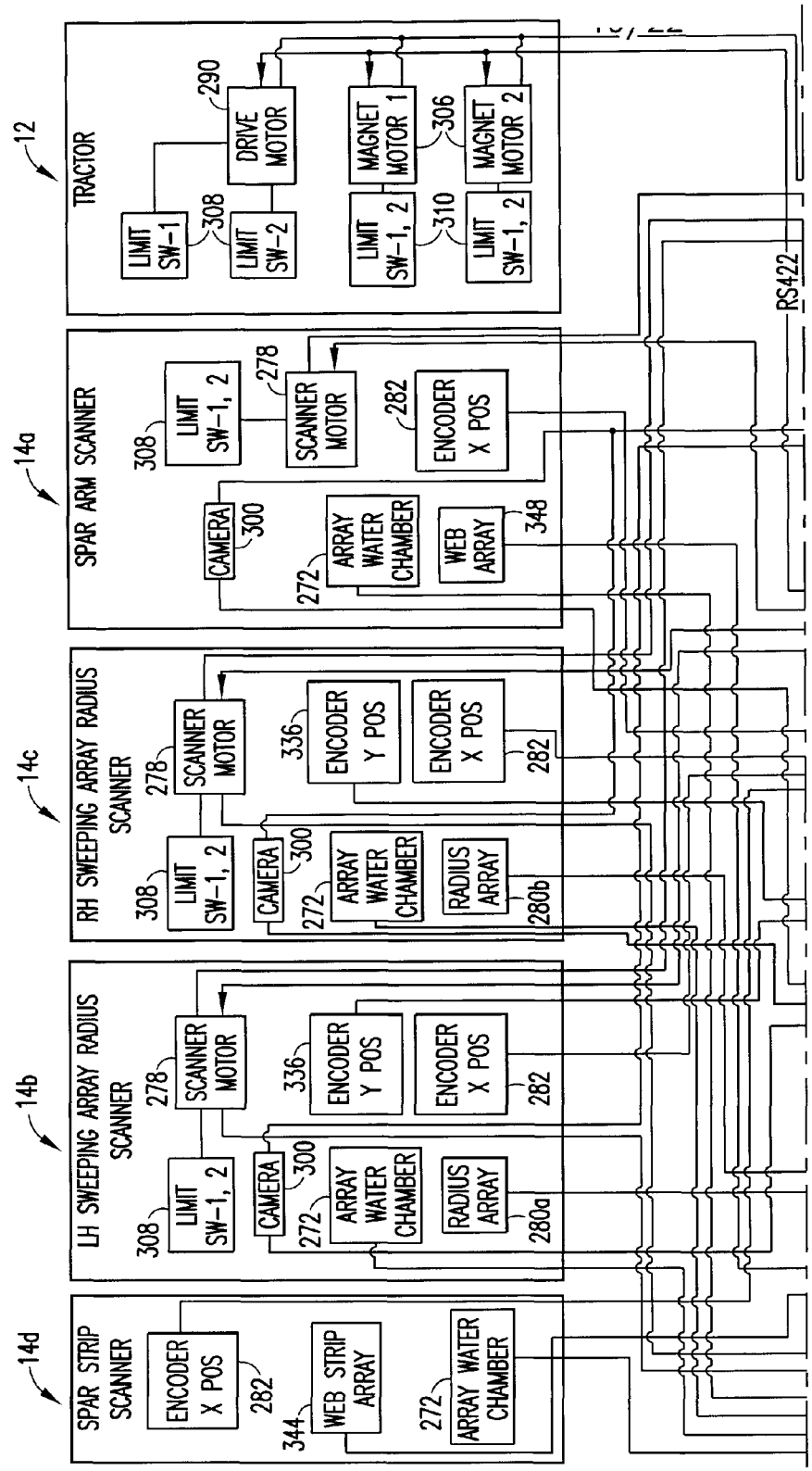

AUTOMATED INSPECTION OF SOFT-TOOLED HOLLOW STRUCTURE

BACKGROUND

This disclosure generally relates to non-destructive inspection (NDI) equipment and methods, and deals more particularly with methods and apparatus for inspecting a soft-tooled hollow structure, especially an elongated hollow structure made of composite material.

A variety of elongated composite structures may have relatively confined internal cavities that require inspection in order to assure that the structure meets production and/or performance specifications. One known elongated composite structure with tapering internal cavities is an integrally stiffened wing box for an airplane. One example application is in the horizontal stabilizer of an aircraft. A horizontal stabilizer structural box may be fabricated as a large co-cured structure that requires the use of soft internal tools to facilitate tool removal after the cure. If a given co-cured composite structure is considered primary structure, it would therefore need to be inspected to ensure structural integrity. Inspecting large soft-tooled composite structures presents four distinct yet interrelated challenges.

(1) Access: The interior of the part is often inaccessible to conventional ultrasonic scanning systems. Equipment and techniques are needed to transport the ultrasonic probes through the interior of the structure.

(2) Coverage: The entire interior surface of the structure needs to be inspected. While equipment and techniques can be used to transport ultrasonic probes to all parts of the structure in a global sense, there is a further need for specialized positioning hardware and techniques to ensure that locally, complete coverage is provided.

(3) Rate: The production manufacturing of structure for an active airplane program needs to be done at a rate that meets schedule commitments. Inspection of primary structure is a necessary part of the manufacturing process and must be done at a rate capable of keeping up with the published schedule.

(4) Conformity: Soft-tooled composites as opposed to hard-tooled composites have surfaces, particularly filleted join regions (referred to herein as "radii"), that are not precisely defined. That is, a designed nominal radius of 0.5 inch will, after fabrication, end up with a "radius" that is not truly circular, being approximated by a spline curve, but possibly with a radius that varies from its nominal value. This is an effect of the soft-tooled fabrication process. In addition, this manufacturing process does not turn out "radius" surfaces that are identical from radius to radius or from part to part. There is inherent variation in the manufacturing process that the ultrasonic inspection equipment and techniques need to take into account. This fabrication variation has special implications for ultrasonic inspection of composite structure because to get acceptable inspection of the interior of the composite part, the ultrasound beam should enter normal or near normal to the front surface of the part. This is because if the beam strikes the front surface at an angle, it will be refracted off normal and a return echo from any possible internal structure or anomaly will not occur. This normality requirement is complicated by the inherent part variations, which means that to ensure sound normality, NDI equipment and techniques should be designed to accomplish this.

Accordingly, there is a need for a system for inspecting the interior of a wing box and similar elongated hollow structures that has the foregoing capabilities.

SUMMARY

The subject matter disclosed herein includes equipment, inspection techniques and inspection sequencing that allow difficult-to-access areas inside an elongated hollow composite structure to be inspected at a production rate. The system disclosed herein is modular and can be transported to and set up in a building or factory with minimal effort.

A system and sequence that allow inspection of elongated hollow structures made of composite material, such as a horizontal stabilizer of an aircraft. The horizontal stabilizer comprises top and bottom skins connected by a plurality of spaced spars. The system employs a plurality of scanners for inspecting different portions of each spar, including a radius scanner specifically designed to inspect the variable radius produced by soft tooling. The system uses dynamically controlled magnetic coupling to connect an external drive tractor to internally placed and computer-controlled scanners that carry respective sensors, e.g., linear ultrasonic transducer arrays. A system operator can control the various components by means of a graphical user interface comprising multiple interaction regions (e.g., buttons) that represent the individual motion paths and are associated with respective motion script files. The inspection methodology was specifically designed to meet the rate needs of the production system.

One aspect of the subject matter disclosed herein is a method for scanning spars of a hollow structure, each spar comprising first and second filleted join regions connected by a web. The method comprises: (a) moving a first sensor along the first filleted join region; (b) actuating the first sensor to transmit beams into the first filleted join region during step (a); (c) moving a second sensor along a first strip-shaped area of the web adjacent to the first filleted join region; (d) actuating the second sensor to transmit beams into the first strip-shaped area during step (c); (e) moving a third sensor along a second strip-shaped area of the web that is not adjacent to the first filleted join region; and (f) actuating the third sensor to transmit beams into the second strip-shaped area during step (e). Steps (a) through (f) can be performed for each of a plurality of spars of the hollow structure, In accordance with a further aspect, the method described in the preceding paragraph further comprises: placing the hollow structure on first and second support tools which are configurable before any of steps (a) through (f) are performed; and changing the configuration of the first support tool from a first configuration to a second configuration after steps (a) through (f) have been performed for the first spar and before any of steps (a) through (f) are performed for the second spar.

Another aspect of the disclosed subject matter is a motion control system comprising: a first scanner that is movable along any one of a first plurality of motion paths within a hollow structure; a command library comprising a first plurality of motion script files containing sequences of commands and parameters respectively associated with the first plurality of motion paths; a graphical user interface comprising a row of tabs that access custom control windows for individual scanner devices, the first window comprising a graphical depiction of one end of the hollow structure and a first plurality of interaction regions (e.g., buttons) inside the graphical depiction of the one end of the hollow structure, the position of each interaction region of the first plurality of interaction regions relative to the graphical depiction of the hollow structure indicating the respective position of the first scanner relative to the hollow structure for a respective motion path of the first plurality of motion paths; and a computer system programmed to execute the sequences of commands in a motion script file corresponding to a selected one of the first plurality of interaction regions, thereby causing the first scanner to move along the corresponding motion path in accordance with its associated parameters.

A further aspect is a system comprising: a tractor comprising a frame, a plurality of wheels rotatably mounted to the frame, a drive motor, first and second magnets, first and second magnet motors, and magnet and X-position limit switches; a plurality of scanners, each scanner comprising a frame, a plurality of wheels rotatably mounted to the frame, first and second magnets arranged for magnetic coupling with the first and second magnets of the tractor, and an X-position encoder; an electronics box comprising a serial interface, a power supply, a power control switch electrically coupled to the power supply and to the serial interface, an X-position encoder selector, and a data acquisition device electrically coupled to the X-position encoder selector; a tractor cable comprising a first plurality of electrical conductors connecting the drive motor and first and second magnet motors of the tractor to the power control switch, a second plurality of electrical conductors connecting the drive motor to the serial interface, and third and fourth pluralities of electrical conductors connecting the third and fourth magnet motors to the serial interface; a plurality of scanner cables respectively connected to the plurality of scanners, each scanner cable comprising a respective electrical conductor connecting a respective X-position encoder attached to a respective scanner to the X-position encoder selector, and the data acquisition device; and a computer system electrically coupled to the data acquisition device and to the serial interface, wherein the computer is programmed to control the states of the power control switch and the X-position encoder selector via the serial interface, and is further programmed to control the drive motor and first and second magnet motors via the serial interface and the second through fourth pluralities of electrical conductors in dependence on scanner X-position information derived by the data acquisition device from pulses generated by one of the X-position encoders.

Other aspects of the invention are disclosed and claimed below.

BRIEF DESCRIPTION OF THE DRAWINGS

FIG. 1 is a diagram showing an orthographic view of a portion of a generalized horizontal stabilizer of an airplane having top and bottom skins or panels connected by a plurality of spars.

FIGS. 2A-2C are diagrams of an end view of a generalized wing box showing the respective positions of three magnetically coupled vehicles during scanning of the following portions of a spar web: (A) a central portion; (B) an edge or marginal portion; or (C) a radius.

FIG. 3 is a diagram showing side views of a tractor-trailer configuration having means for adaptive magnetic coupling. A second trailer vehicle is not visible. The left-hand side of FIG. 3 shows an inspection scenario wherein the trailer vehicles are inverted, while the right-hand side shows an inspection scenario wherein the tractor vehicle is inverted.

DETAILED DESCRIPTION

Figure 4:
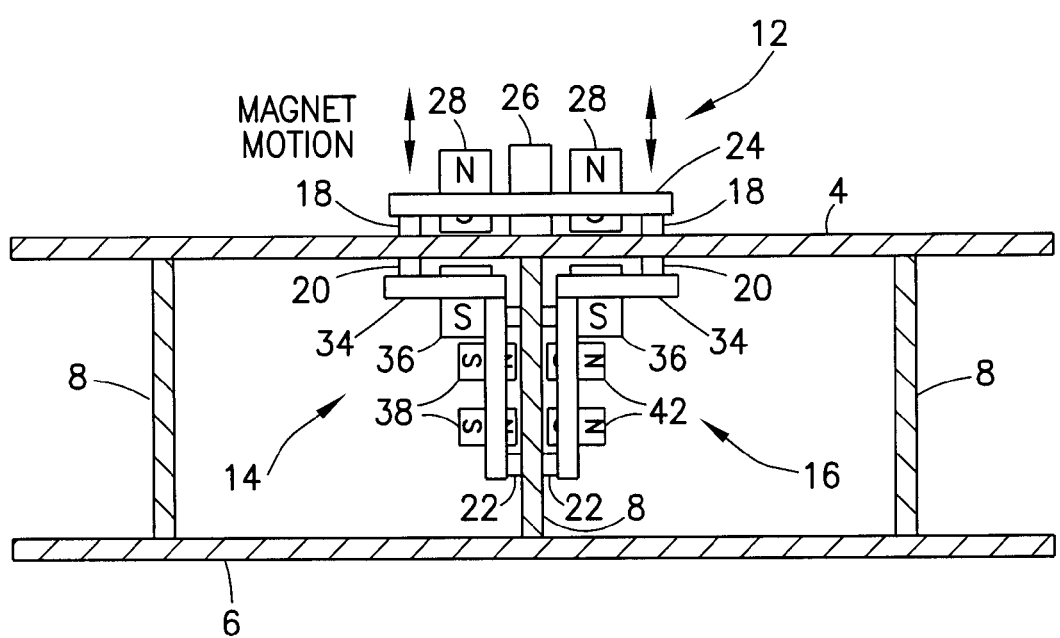
FIG. 4 is a diagram showing an end view of the tractor-trailer configuration depicted on the left-hand side of FIG. 3 (with respective inverted trailer vehicles disposed on opposing sides of a spar).

In accordance with one embodiment, ultrasonic NDI sensors are used to inspect a hollow composite structure, such as an integrally stiffened wing box for an aircraft (e.g., a horizontal stabilizer). A portion of a generalized integrally stiffened wing box 2 for an aircraft is depicted in FIG. 1. The depicted integrally stiffened wing box comprises a top skin 4 and a bottom skin 6 connected by a plurality of a plurality of internal vertical support elements, hereinafter referred to as "spars". Each spar comprises a web 8 and respective pairs of filleted join regions 10 (also called "spar radii"), which connect the spar web 8 to the top and bottom skins. As used herein, the terms "top skin" and "bottom skin" refer to the relative positions of two skins of a wing box when the wing box is being inspected, not when the wing box is installed on an airplane (i.e., a wing box may be inverted for inspection).

In accordance with one embodiment, an ultrasonic linear array (i.e., sensor) is transported down the length of a tunnel through the interior of the composite structure. For this type of inspection, the sensor is carried by a trailer vehicle (not shown in FIG. 1) placed inside the hollow structure 2. This trailer vehicle can be characterized as being "active" in the sense that equipment it carries is actively performing a scanning function. The sensor needs to be acoustically coupled to each surface being inspected while an automated tractor vehicle (also not shown in FIG. 1) moves the trailer vehicle along that surface in a region of interest. This is accomplished by providing a column of water that flows between the sensor and the inspected part.

In FIG. 1, portions of the interior surfaces of the part which need to be inspected can be seen. Each spar needs to have all four filleted join regions 10 and each web 8 inspected. This is a challenging inspection as each cavity is essentially a long rectangular tunnel that decreases in cross section as one moves from root to tip. The top and bottom skins 4 and 6 can be inspected from the exterior using conventional NDI techniques.

The basic integrated inspection system consists of several parts, each of which will be described in detail. The different parts are as follows: (1) an external motorized tractor used to move an internal active trailer that carries a sensor and a passive trailer through the part being inspected; (2) a part holding fixture designed to have channels that allow the tractor to run along the length of part on its bottom; (3) a strip scanner used to inspect the edges of a spar web; (4) a spar arm scanner used to inspect a central part of the web; (5) a radius scanner used to inspect a radius; (6) a cable management system used to automatically handle the various cables; (7) an electronic control box used to select which sensor and other system components are active and provide power, etc.; (8) motion control software; (9) ultrasonic data acquisition and analysis software; (10) a computer that hosts the ultrasonic analysis, data acquisition and motion control software; and (11) ultrasonic instruments used for data acquisition.

All of these are components of an integrated system that, when used with a sequencing flow developed for this equipment, allows hollow composite parts to be inspected completely and at a rate that meets production requirements. FIGS. 2A-2C show the various inspections. In each instance, a horizontal motion drive vehicle 12, known as a "tractor", is magnetically coupled to the trailers 14, 16 that travel down the spar in the interior of the part. The trailer vehicles 14, 16, in turn, are magnetically coupled to each other. It should be appreciated that the construction of the trailer vehicles 14, 16 will be different for each of the three inspection scenarios depicted in FIGS. 2A-2C. In each of FIGS. 2A-2C, the sensor (not shown) is carried by a respective trailer vehicle 14. The transmitted beam is indicated by a dashed arrow.

FIG. 2A shows the respective positions of the vehicles during inspection of a central area A of a spar web 8. For the inspection depicted in FIG. 2A, the trailer vehicle 14 will take the form of a spar arm scanner (described in detail below). The tractor vehicle 12 is placed below the bottom skin 6.

FIG. 2B shows the respective positions of the vehicles during inspection of an upper edge area B of a spar. For the inspection depicted in FIG. 2B, the trailer vehicle 14 will take the form of a spar strip scanner (described in detail below). To inspect the lower edge area, the vehicles will be placed in the same positions seen in FIG. 2A.

FIG. 2C shows the respective positions of the vehicles during inspection of an area C that includes an upper filleted join region 10. FIG. 2C depicts a situation wherein the upper filleted join region is being inspected from the right-hand side of the spar. For the inspection depicted in FIG. 2C, the trailer vehicle 14 will take the form of a radius scanner (described in detail below). The upper filleted join region will also be inspected from the left-hand side of the spar web. In the latter situation, a different radius scanner is used and the positions of trailers 14, 16 will be reversed. Inspection of the lower filleted join region 10 from both sides of the spar web 8 can be performed using the same two radius scanners.

Tractor/Trailer Transport System

In accordance with one embodiment for inspecting structures of the type shown in FIGS. 1 and 2A-2C, an external motorized and computer-controlled tractor 12 is magnetically coupled to an internal active trailer 14 that holds and positions an ultrasonic transducer array on the interior of the part. Also, there is an internal passive trailer 16 on the opposite side of the spar that is magnetically coupled through the spar to the active trailer 14 and also magnetically coupled through the skin to the tractor 12. This three-part system gives a very stable system for positioning and moving the ultrasonic transducers.

FIG. 3 shows side views of a tractor-trailer configuration in accordance with one embodiment in two different inspection situations (motor actuators are not shown). The automated NDI inspection system comprises a traction-motor powered tractor vehicle 12, which rides on the external surface of top skin 4 or bottom skin 6 of horizontal stabilizer 2, and a pair of trailer vehicles (only trailer vehicle 14 is visible in FIG. 3, the other being hidden behind a spar web 8), which ride along an internal surface of the top or bottom skin. The left-hand side of FIG. 3 shows an inspection scenario wherein the tractor vehicle 12 is outside the horizontal stabilizer in a non-inverted position while the trailer vehicles are inside the horizontal stabilizer in inverted positions; the right-hand side of FIG. 3 shows an inspection scenario wherein the tractor vehicle 12 is outside the horizontal stabilizer in an inverted position while the trailer vehicles are inside the horizontal stabilizer in non-inverted positions. FIG. 4 shows an end view of the tractor-trailer configuration depicted on the left-hand side of FIG. 3, with inverted trailer vehicles 14 and 16 disposed on opposite sides of a spar.

In the inspection scenario depicted in FIG. 4 (and the left-hand side of FIG. 3), idler wheels 18 of tractor vehicle 12 contact and roll on the external surface of top skin 4 while vertical idler wheels 20 of inverted trailer vehicles 14 and 16 (only one such idler wheel is visible in FIG. 4 for each trailer vehicle) contact and roll on the internal surface of top skin 4, and the horizontal idler wheels 22 roll on the spar surface. The right-hand side of FIG. 3 show an alternative situation wherein idler wheels 18 of the inverted tractor vehicle 12 contact and roll on the external surface of bottom skin 6 while vertical idler wheels 20 of trailer vehicle 14 (and also idler wheels of trailer vehicle 16 not visible in FIG. 3) contact and roll on the internal surface of bottom skin 6, and the horizontal idler wheels 22 roll on the spar surface.

In accordance with the embodiment partly depicted in FIGS. 3 and 4, the tractor vehicle 12 comprises a frame 24. Four idler wheels 18 (only two of which are visible in each of FIGS. 3 and 4) are rotatably mounted to frame 24 in a conventional manner. (Alternative embodiments may include more idler wheels.) The idler wheels 18 are made of plastic and have smooth contact surfaces. Tractor vehicle motion is enabled by driving a drive wheel 26 (also rotatably mounted to frame 24) to rotate. Drive wheel 26 is coupled to a motor 30 via a transmission (not shown). The drive wheel 26 is positioned on the frame 24 so that it is in frictional contact with skin 4 or 6 when idler wheels 18 are in contact with the same skin. The drive wheel is made of synthetic rubber material. The surface of the drive wheel may have a tread pattern. In addition, the tractor vehicle 12 carries multiple permanent magnets 28. Each permanent magnet 28 has North and South poles, respectively indicated by letters "N" and "S" in the drawings.

Still referring to FIGS. 3 and 4, each trailer vehicle 14, 16 is comprised of a respective frame 34. For each trailer vehicle, two vertical idler wheels 20 (only one of which is visible in FIG. 4) and four horizontal idler wheels 22 (only two of which are visible in FIG. 4) are rotatably mounted to frame 34 in a conventional manner. (Alternative embodiments may include more idler wheels.) Each trailer vehicle 14, 16 carries multiple vertically mounted permanent magnets 36, the North poles of which are magnetically coupled to the South poles of confronting permanent magnets 28 carried by the tractor vehicle 12. In the design described by FIGS. 3 and 4, each trailer has two vertically mounted permanent magnets 36, but other designs may use different configurations. The positions and pole orientations of the magnets may have other configurations as long as the N-S pairing and relative alignment of the magnets between the tractor and trailer are preserved.

As seen in FIG. 4, in addition to being magnetically coupled to the tractor vehicle 12, the trailer vehicles 14 and 16 are magnetically coupled to each other using additional sets of permanent magnets 38 and 42. As seen in FIG. 3, trailer vehicle 14 carries four horizontally mounted permanent magnets 38. Trailer vehicle 16 also carries four horizontally mounted permanent magnets 42 (only two of which are visible in FIG. 4), the poles of which are respectively magnetically coupled to opposing poles of the permanent magnets 38 on trailer vehicle 14. This magnetic coupling produces an attraction force that holds idler wheels 22 of trailer vehicles 14 and 16 in contact with opposing surfaces of an intervening spar web 8 (shown in FIG. 4).

As seen in FIG. 3, trailer vehicle 14 further carries a payload 40. Three specific embodiments of trailer vehicle 14 (respectively named spar strip scanner, spar arm scanner and spar radius scanner) will be described in detail below. In each implementation, an NDI sensor is acoustically coupled to the internal surface being inspected. For example, the inspected region may be covered with a continuous stream of water to acoustically couple the ultrasonic sensor to a spar web 8 or a filleted join region 10. Magnetically coupled systems are well suited for operation with water in the environment. The orientation and scanning movement of payload 40 will depend on which portion of the horizontal stabilizer internal surface is to be inspected.

As the tractor vehicle is driven to travel along a desired path on the outer surface of the top or bottom skin, it pulls the inner trailer vehicles along. The magnetic coupling system described above keeps the inverted vehicle(s) in contact with the surface it rides on. For horizontal stabilizer applications, two magnetically coupled trailer vehicles can be used, one on each side of the spar web 8, as shown in FIG. 4. This allows the system to take advantage of the internal structure of the scanned object as a guide to allow the system to track properly along the surface.

The tractor has the ability to vary the amount of magnetic coupling force by physically moving the magnets farther apart using motors that are under computer control. This allows the apparatus to match the magnetic coupling force to the thickness of the part being inspected. In this case, as the part thickness varies along the length of the part, the magnetic coupling force is dynamically adjusted under computer control to reflect this. A feedback sensor is needed to provide information required by the control computer to adjust the magnet separation distance as the skin thickness varies. One sensor option is a wheel rotation encoder rotatably mounted to the frame of one of the trailer vehicles to provide displacement from a specified starting point along the length of the horizontal stabilizer (or other structure being inspected). This position information, along with predetermined data about the thickness of the skin (either from a CAD model or measured directly), can be used to determine the amount of displacement needed for the movable magnet units on the tractor. By knowing the relative locations of each of the magnetic coupling units to the location of the sensor, the desired separation at each of the magnets can be determined. FIGS. 3 and 4 do not show the means for automatically adapting to the variable thickness of the intervening skin or panel (i.e., top skin 4 or bottom skin 6) by raising or lowering the magnets (which magnet motion is indicated by double-headed arrows in FIGS. 3 and 4) on the tractor vehicle as it moves along the structure being inspected. Further details concerning the trailer-tractor configuration depicted in FIGS. 3 and 4 and other embodiments are disclosed in U.S. patent application Ser. No. 13/313,267, the disclosure of which is incorporated by reference herein in its entirety.

The basic concept of the tractor/trailer transport system described above can be adapted as necessary to perform different scanning operations, such as scanning the edge and central portions of each web 8 and the four filleted join regions 10 that join each web to the top and bottom skins (two at the top skin 4 and two at the bottom skin 6). While it is advantageous to use the same tractor for each of the different scanning operations that make up the overall inspection process, a different active trailer can be used to perform each respective specific scanning operation. This in turn may require the use of a respective passive trailer specifically adapted to magnetically couple with a respective active trailer. This disclosure will describe methods and apparatus for inspecting filleted join regions (hereinafter "radii") of an elongated and tapered hollow structure. The active trailer for scanning a spar radius will be referred to herein as a "spar radius scanner". This disclosure will also describe methods and apparatus for inspecting the central portion of a spar web. The active trailer for scanning the central portion of a spar web will be referred to herein as a "spar arm scanner". In addition, this disclosure will describe methods and apparatus for inspecting the marginal or edge portions of a spar web. The active trailer for scanning the marginal portion of a spar web will be referred to herein as a "spar strip scanner".

Part Holding Tools

Figure 5:
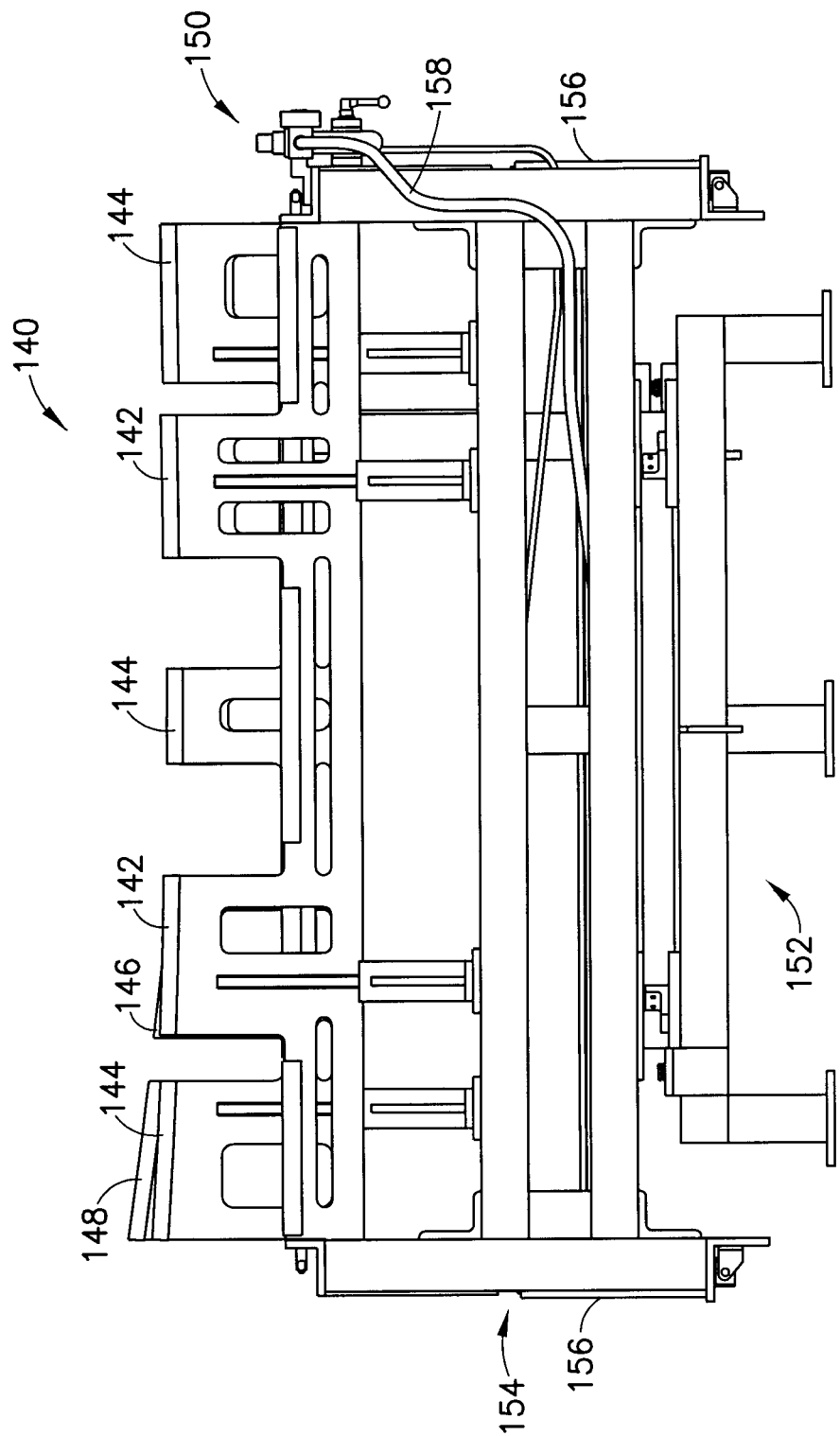
FIGS. 5 and 6 are diagrams showing respective end views of two tools designed to support the root (inboard) and tip (outboard) ends respectively of a wing box during non-destructive inspection using the system disclosed herein.
Figure 6:
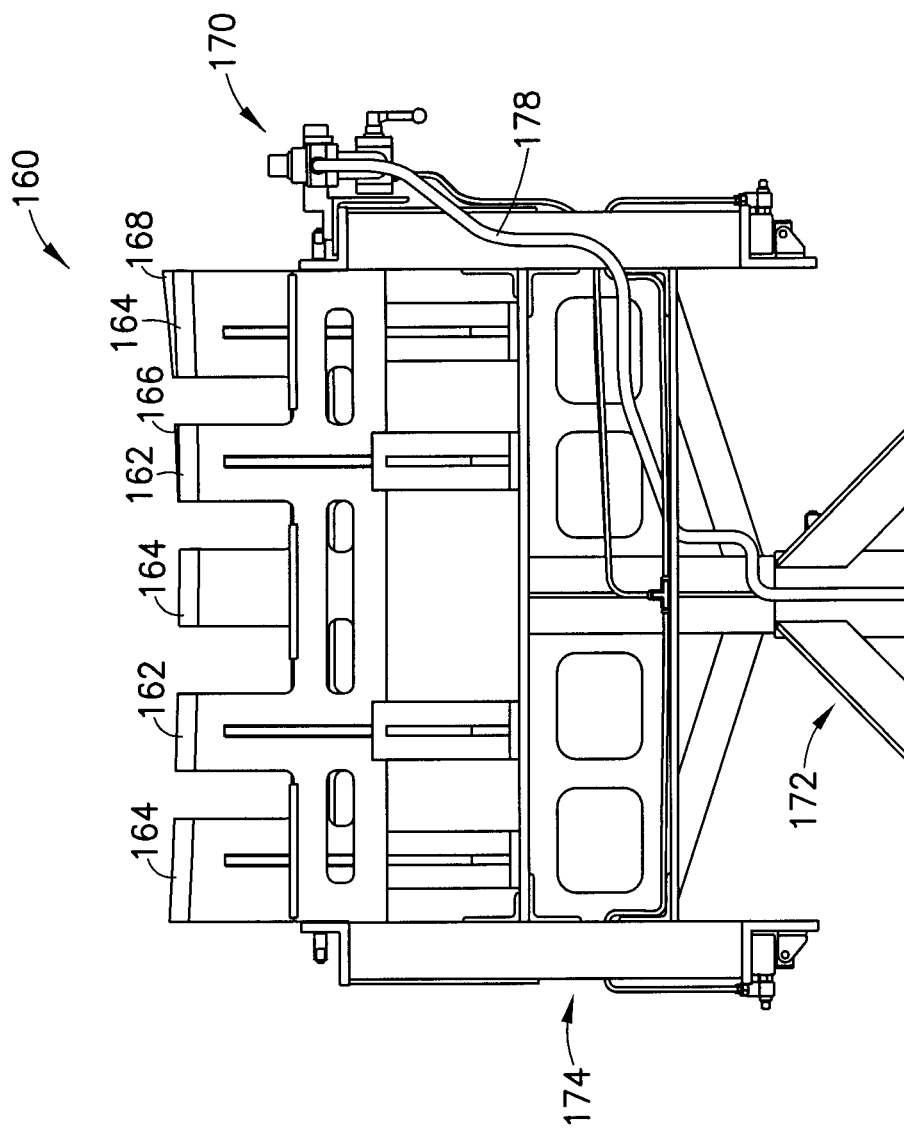

As should be apparent from the above description of FIGS. 2A-2C, a feature of the tractor is that it has the ability to run on the bottom as well as the top of the part being inspected. To run on the bottom, the tractor needs a clear path that avoids any structural supports. As part of this inspection system, a pair of part holding tools were designed that support the part at opposite ends thereof. In particular, in the case where the part being inspected is a horizontal stabilizer, one part holding tool (hereinafter "inboard support tool") 140 depicted in FIG. 5 is designed to hold/support a root end of the horizontal stabilizer. Inboard support tool 140 comprises a pedestal 152 that stands on the ground and a frame 154 supported by the pedestal 152. Another part holding tool (hereinafter "outboard support tool") 160 depicted in FIG. 6 is designed to hold/support a tip end of the horizontal stabilizer, the tip end being narrower than the root end. Inboard support tool 140. Outboard tool 160 comprises a pedestal 172 that stands on the ground and a frame 174 supported by the pedestal 172. Each part holding tool 140, 160 has movable support structure that can be adjusted to provide a clear tractor channel for inspection of the horizontal stabilizer spars.

Although not fully visible in the views of FIGS. 5 and 6, each tool comprises four rows of vertically displaceable headers arranged in sequence, one behind another. The headers are shaped to allow the tractor to pass between the vertical supports, and different headers are used for support at different times, depending on which motion path the tractor is following. From the vantage point of FIG. 5: a first row of two headers 142 is visible in its entirety; three headers 144 of a second row (behind the first row) are visible; portions of two headers 146 of a third row (behind headers 142) are visible; and portions of three headers 148 of a fourth row (behind headers 144) are visible. From the vantage point of FIG. 6: a first row of two headers 162 is visible in its entirety; three headers 164 of a second row (behind the first row) are visible; portions of two headers 166 of a third row (behind headers 162) are visible; and portions of three headers 168 of a fourth row (behind headers 164) are visible.

Each row of headers is attached to and vertically displaceable by pistons of a respective pair of air cylinders 156 situated on opposite sides of the frame 154. The specific embodiment of tool 140 depicted in FIG. 5 has four pairs of four air cylinders 156 arranged in respective rows on opposing sides of frame 154. Only the first pair of air cylinders 156 are partially visible in FIG. 5, with other air cylinders being disposed in respective rows behind the first pair of air cylinders. Each row of headers can be moved up and down independently. Although FIG. 5 depicts all headers in an up position, during inspection of a horizontal stabilizer only a selected single header row is up while the other three are down. For example, headers 142 will be up and headers 144, 146 and 148 will be down when a central spar is being inspected, which arrangement provides clearance for a tractor vehicle to travel underneath that central spar on the bottom skin of the horizontal stabilizer. Similarly, headers 144 will be up and headers 142, 146 and 148 will be down when a spar adjacent the central spar is being inspected, which arrangement provides clearance for the tractor vehicle to travel underneath that adjacent spar. Two rows of headers (142 and 144) are designed to support a horizontal stabilizer in an upright position; the other two rows of headers (146 and 148) are designed to support a horizontal stabilizer in an upside-down position. Headers 142 and 144 match the contour of the upper skin of the horizontal stabilizer; headers 146 and 148 match the contour of the lower skin. The headers 162, 164, 166 and 168 of tool 160 are configured and operated in a similar way.

Referring again to FIG. 5, each air cylinder 156 can be selectively supplied with pressurized air from a source via an air distribution system 158 (only partly visible in FIG. 5). The air cylinders are actuated in pairs by manual operation of header controls 150. For example, to achieve a tool state where only headers 142 are up, the header controls 150 are operated to open/close valves as necessary to provide pressurized air from a source to only that pair of air cylinders capable of lifting the row of headers 142. Similarly, outboard support tool 160 comprises an air distribution system 178 (only partly visible in FIG. 6) that supplies pressurized air from the source to a pair air cylinders capable of lifting whichever row of headers has been selected by manual operation of header controls 170.

Spar Web Scanning

The interior inspection of the spar radii and web covers the entire surface area. In accordance with one implementation, the horizontal stabilizer is inspected while its root end is in an untrimmed condition, indicated by a solid vertical line on the far left of FIG. 7. The dashed vertical line indicates the location of the root end of the horizontal stabilizer after trimming. Thus the area of the spar between the solid and dashed vertical lines in FIG. 7 need not be inspected.

Figure 7:
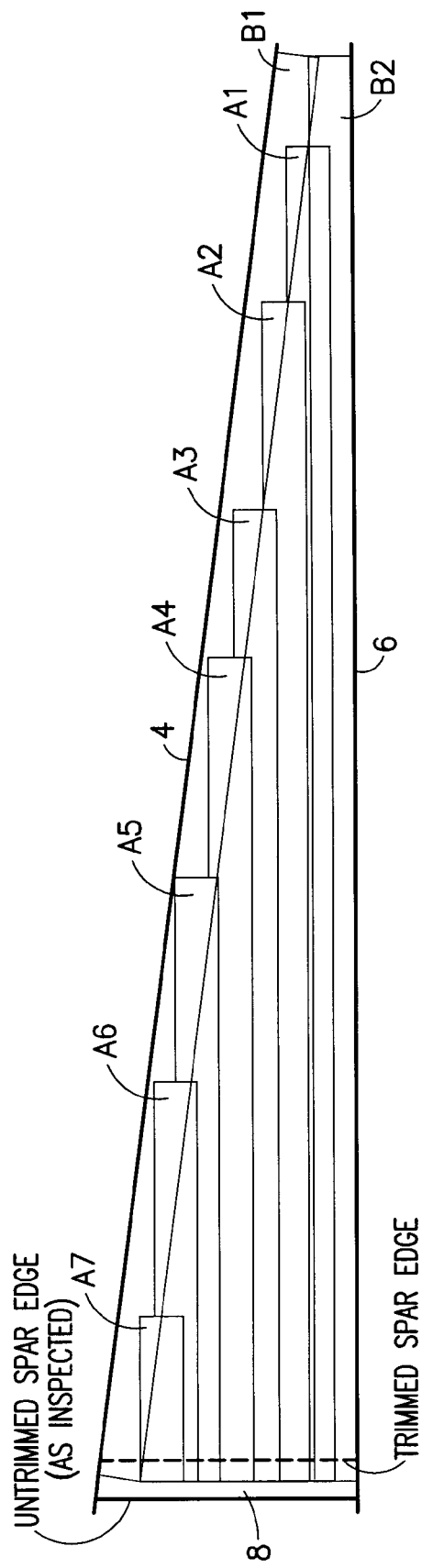
FIG. 7 is a diagram showing spar web and edge area scan coverage in accordance with one implementation.

The spar web is scanned by a two-part inspection system that covers two distinct zones: a strip along the spar web next to a radius and a central portion of the spar web. FIG. 7 illustrates this concept of covering the spar web. As seen in FIG. 7, the central portion of the spar web is scanned by a spar arm scanner (not shown in FIG. 7) that covers successive horizontal strips A1 through A7 that overlap in multiple passes. The spar web changes shape as it goes from root to tip. This is further complicated by the soft-tooled aspects of the part and the geometric variations that are inherent in the manufacturing process of such a part. The solution includes a spar strip scanner (not shown in FIG. 7) that scans narrow (e.g., 2-inch) strips at the top and bottom edges of the spar web (see strips B1 and B2 in FIG. 7). The strip scanner is designed to mechanically follow the contour of the adjacent skin and hold itself against the breakpoint of the radius so that no prior detailed information of the part geometry is required.

The spar strip scanner and spar arm scanner use identical linear ultrasonic transducer arrays that cover a scan strip of the same width (e.g., 2 inches). These sensors are used in pulse echo mode, which means they both transmit and receive. This means that a separate ultrasound array for receiving is not needed. Each of the spar strip and arm scanners is connected to a data acquisition computer via a respective cable that contains data lines, a water line and various sensor lines. The sensors coupled to the inspected part use water that is supplied from the cable water line as an acoustic couplant. Each sensor is held in a "shoe" that ensures the array is mechanically positioned relative to the spar surface. In addition, the shoe has a water-filled cavity situated between the sensor and spar, which cavity guides the water that flows therethrough.

Spar Strip Scanner

Figure 8:
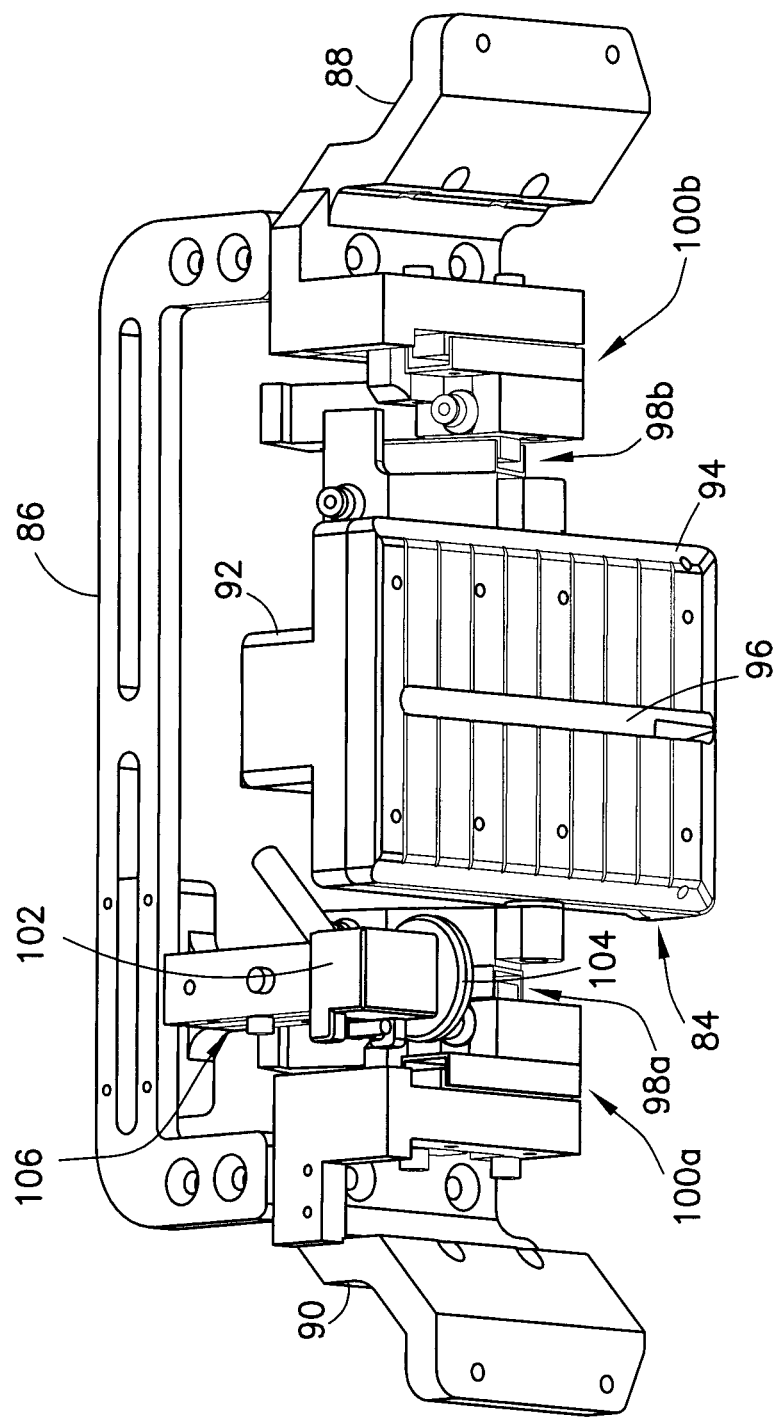
FIG. 8 is a diagram showing an isometric view of portions of a strip scanner in accordance with one embodiment.

The spar strip scanner can be used on both the top and bottom edges of the spar web (see strips B1 and B2 in FIG. 7) and has the ability to reverse the connection cable direction, which is necessary when going from a top to a bottom edge inspection. The strip scanner inspects close to both ends of the spar. One embodiment of the strip scanner comprises a linear ultrasonic transducer array which is incorporated in a probe assembly that is connected at opposite ends to respective sets of magnet trolleys which carry magnets for magnetically coupling the strip scanner with a tractor vehicle and a passive trailer vehicle in the manner previously described. FIG. 8 shows one embodiment of such a strip scanner with the magnet trolleys omitted.

In accordance with the embodiment partially depicted in FIG. 8, the strip scanner carries a probe assembly 84 that operates as previously described under the control of a computer that hosts data acquisition/analysis software. The strip scanner may also have a video camera (not shown) that captures a live view of the probe. The X-axis motion (the X axis being parallel to the spar radius being inspected if the path is linear in the lengthwise direction of the filleted join region) is provided by the tractor vehicle of the system, which uses data from a rotational encoder 102 coupled to an encoder wheel 104. The strip scanner is pulled by the tractor and carries the probe assembly 84. The probe assembly comprises a probe body or shoe 92 that holds a linear ultrasonic transducer array (not visible in FIG. 8) and has a water cavity 96 disposed between the array and the plane of a wear surface 94 which will be in contact with the surface of the spar web edge being scanned.

In the embodiment partially depicted in FIG. 8, the probe assembly 84 is not directly displaced by a motor, but is supported by an assembly of components which allow the probe assembly to passively adjust its position while held in contact with internal surfaces of the spar web and adjacent skin. The support assembly supports the probe assembly 84 by means of four linear motion guides (each guide comprising a respective pair of slidably coupled linear motion guide halves), including two Z-axis linear motion guides 98*a,b* and two Y-axis linear motion guides 100*a,b*. As used herein, the term "linear motion guide half" means a structure having a straight surface that guides a contacting surface of another linear motion guide half to move linearly during relative motion of the two halves. More specifically, the term "linear motion guide half" includes, but is not limited to, male and female slide halves well known in the art.

The Z-axis linear motion guides 98*a,b* allow the probe assembly 84 to displace back and forth along a local Z axis which is not normal to the opposing spar web surface (which takes into account that the skin portion adjacent the spar web edge may be at an acute angle). The Y-axis linear motion guides 100*a,b* allow the probe assembly 84 to displace back and forth along a local Y axis which is in the plane of the spar web and perpendicular to the X axis. Respective pairs of springs (not shown in FIG. 8) are provided to bias the probe assembly 84 toward the corner formed by the spar web edge and adjacent skin portion, thereby maintaining the wear surface 94 of probe assembly 84 in contact with the spar web edge to be scanned.

Figure 20:
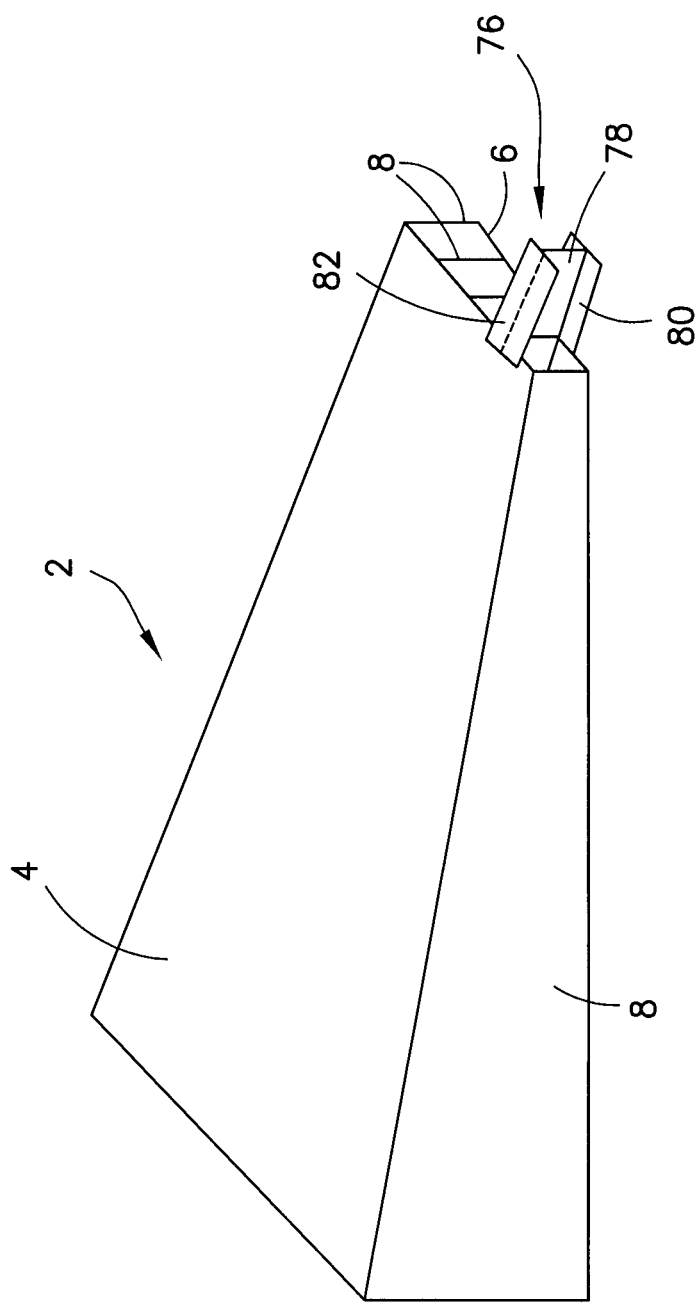
FIG. 20 is a diagram showing an isometric view of a generalized wing box having a runoff component attached thereto.

The support assembly further comprises a bridge 86 that is connected at opposite ends thereof to respective support members 88 and 90 which will be fastened to the respective sets of magnet trolleys. The encoder wheel is rotatably coupled to an X-position rotational encoder 102 which, in turn, is slidably coupled to the bridge 86 by means of an encoder linear motion guide 106. The encoder linear motion guide 106 allows the encoder/encoder wheel subassembly to displace back and forth along a true Z axis which is perpendicular to the X-Y plane. A spring (not shown in FIG. 8) is provided to hold the encoder wheel in contact with the surface of the spar web edge. The sensor need not move relative to the platform during edge scanning, so the strip scanner does not need to be equipped with a motor. For the sensor to reach the end of the part, the transporting mechanism would need to start slightly off the end of the start position and then run slightly off the end of the finish position. To accomplish this, run-on and run-off components can be used to allow the tractor and trailer vehicles to start partially off of the part being inspected and to run partially off the end of the part. These components will be respectively attached to the start and end positions and will allow the centrally mounted sensor to cover the entire length of the spar. The run-on and run-off components (which may be made of plastic or composite material) are sized and shaped to match the particular spar being inspected and are different for the root and tip ends of the wing box. They may be clamped or taped in place. One embodiment of such a runoff component 76 is shown in FIG. 20. This runoff component 76 comprises a spar web 78, a bottom skin 80 and a top skin 82, which are respectively aligned with the spar web 8, bottom skin 6 and top skin 4 of the wing box being inspected.

An alternative way to allow the centrally mounted sensor to cover the entire length of the spar is to start with the spar strip scanner not completely on the spar and with the back set of passive magnets not attached and then manually "walk" the strip scanner onto the spar, attaching the rear passive trailer magnets when the strip scanner is completely on the part. This sequence would be reversed at the strip scanner end position to ensure that the inspection goes to the end of the part.

Another way to ensure that the edges of the spar web are inspected by the strip scanner is to use two sensors, with one mounted at each end of the strip scanner. This embodiment of the strip scanner has a pair of probe assemblies (not shown) carried by a suitable support structure. This design enables the strip scanner to inspect the spar web from end to end, since it can move equally well in either direction.

Spar Arm Scanner

The central part of the spar web is inspected with a scanner that comprises a computer-controlled collapsible lifting arm having a distal end which carries the sensor and can be positioned at various commanded heights (hereinafter referred to as a "spar arm scanner"). The spar arm scanner can perform a raster scan of the central area of the spar web under computer control. As previously described, the strip scanner mechanically follows the edge of the spar web next to a radius over a strip-shaped area of constant width (e.g., 2 inches). Therefore, the arm scanner need not position the sensor it carries particularly close to the radius. This significantly lessens the motion control complexity as compared to what would be entailed if the "buffer" strips (B1 and B2 in FIG. 7) where not covered by a separate scanner. In addition, the arm scanner always positions the sensor toward the wide or root end of the spar. This means that scanning the root end of the spar is not an issue. The tip end of the spar does not need its edge to be scanned because at this point, overlapping strip scans have this area covered. Advantageous features of this spar arm scanner include at least the following: (1) the ability to collapse the arm to a very low height to pass through narrow sections of a horizontal stabilizer, and also extend the arm by more than a factor of three to reach the maximum height of the horizontal stabilizer tunnels; and (2) the vertical position measurement and control process developed for the arm scanner uses kinematic equations of motion and data from a standard rotational encoder on the motor to determine vertical position and to enable vertical position control. These features allow the system to work within the physical size limitations of hollow structures like a horizontal stabilizer, while also allowing the system to be operated in wet environments associated with ultrasonic-based NDI scanning.

Figure 9A:
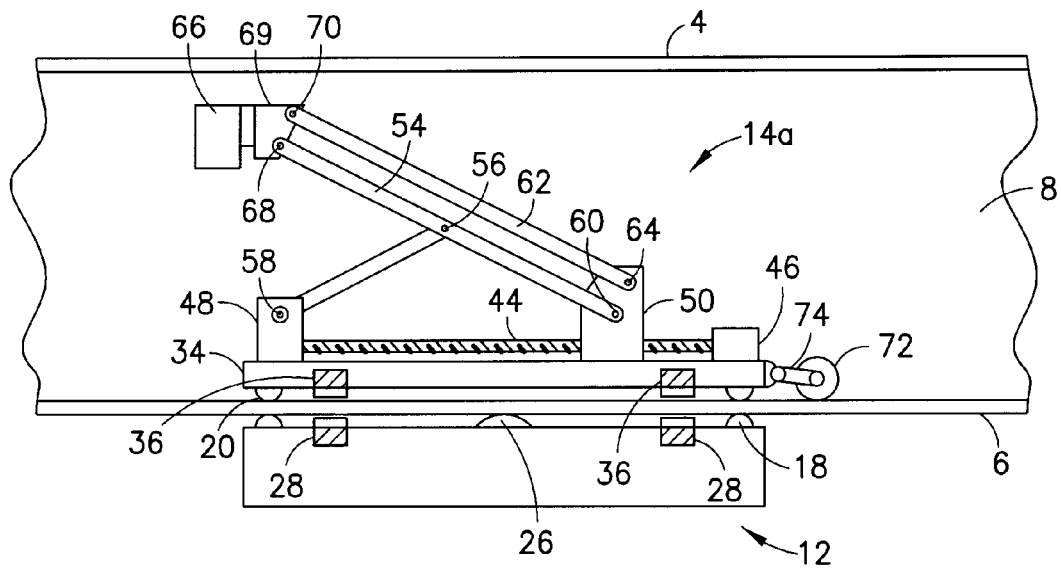
FIG. 9A is a diagram showing a side view of a tractor-trailer configuration that includes active and passive trailer vehicles above (the passive trailer is hidden behind the spar web) and a tractor vehicle below a bottom skin of a wing box. In accordance with one embodiment, the active trailer vehicle comprises a scissors lift mechanism with an additional four-bar parallelogram linkage for vertically displacing a payload while keeping the payload orientation constant.

The spar arm scanner operates under computer control within vertical height restrictions and in wet environments. FIG. 9A is a side view showing one embodiment of a spar arm scanner 14*a* magnetically coupled to a tractor vehicle 12. A passive trailer vehicle 16 (not visible in FIG. 9A) can be seen in the end view of FIG. 9B.

Arm Motion.

Referring to FIG. 9A, the spar arm scanner 14*a* is magnetically coupled to and pulled by tractor 12. The arm scanner 14*a* comprises magnets 36 which are coupled to opposing tractor magnets 28 through a bottom skin 6. Trailer-to-trailer coupling magnets are also part of the system, but are not shown in FIG. 9A. The spar arm scanner 14*a* carries a payload 66 for non-destructive inspection of a web 8. The X-position of arm scanner 14*a* (and the payload it carries) is measured by an X-direction encoder (not shown in FIG. 9A), which measures the rotation angle of an encoder wheel 72 mounted on the end of an encoder swing arm 74. The encoder swing arm 74 is pivotably coupled to trailer frame 34*a* of arm scanner 14*a*. The encoder wheel 72 rides on the inner surface of the bottom skin 6 as arm scanner 14*a* travels along a filleted join region.

The spar arm scanner in accordance with the embodiment shown in FIG. 9A further comprises a modified single-stage scissor lift mechanism (also known as a scissor linkage mechanism) with one degree of freedom, which is driven by a lead screw 44 and a programmable stepper motor 46. The modified scissor lift mechanism comprises a support block 48 mounted to a vehicle frame 34*a* and a translatable (relative to frame 34*a*) support block 50 (hereinafter "slider mechanism"). The lead screw 44 has a distal end rotatably coupled to support block 48 and an intermediate portion rotatably coupled to slider mechanism 50 by a nut (not shown), which is attached to the latter. The stepper motor 46 is mounted to frame 34a. An output shaft of stepper motor 46 is coupled to the other end of lead screw 44. The slider mechanism 50 is put into motion by means of the lead screw 44 and stepper motor 46.

The modified scissor lift mechanism further comprises one link 52 having a length half that of another link 54. Link 52 is attached to a pivot point (first revolute joint) 56 midway along the length of the longer link 54, which will be referred to hereinafter as the "drive link". [A revolute joint (also called pin joint or hinge joint) is a one-degree-of-freedom kinematic pair used in mechanisms. Revolute joints provide single-axis rotation.] The other end of the shorter link 52 is pivotably coupled to support block 48 by a second revolute joint 58, and one end (referred to herein as the proximal end) of the drive link 54 is pivotably coupled to slider mechanism 50 through a third revolute joint 60. The slider mechanism 50 moves joint 60 towards or away from joint 58. The motion path of block 50 is a straight line defined by the axis of lead screw 44. In this configuration, the motion of the proximal end of drive link 54 causes orthogonal motion of its other end (referred to as the distal end) relative to the motion of the slider block 50. For the measurement task that this system is has been designed for, the proximal end of the drive link being driven by the lead screw moves horizontally, while the distal end moves vertically.

Although the position paths that both the proximal and distal ends of the drive link segment take are both linear (i.e., perfectly horizontal and perfectly vertical, respectively), the relative relationship between input and output velocities is not linear. This non-linear relationship between the input and output velocities has an impact on the motion control of this system, which will be described in detail later.

In addition to the long and short links of the single-stage scissor lift mechanism, a follower link 62, of equal length to drive link 54, is used to form a four-bar parallelogram linkage with the drive link 54 as one of the links. (This aspect of the system produces a "modified scissor lift mechanism", as described herein.) This additional link allows the system to maintain a constant orientation of the payload platform 69 located at the distal end of the drive link. Follower link 62 is pivotably coupled to slider mechanism 50 by a revolute joint 64. The payload platform 69 is pivotably coupled to the distal ends of links 54 and 62 by respective pin joints 68 and 70. During operation, as the proximal end of drive link 54 is driven by lead screw 44 from one end point of travel to the other, the payload platform motion will always stay perpendicular to the lead screw 44 and the orientation will stay constant. In other words, as slider mechanism 50 is moved toward support block 48, payload 66 (which is attached to the payload platform 69) moves up along a vertical path without rotating. In the current implementation of this design, the lead screw 44 is installed in parallel with the vehicle frame 34a, resulting in motion of the payload platform 66 being perpendicular to the frame 34a, which itself rides on wheels 20 that position the frame 34a parallel to the surface of the object being scanned.

Chassis Motion.

Figure 9B:
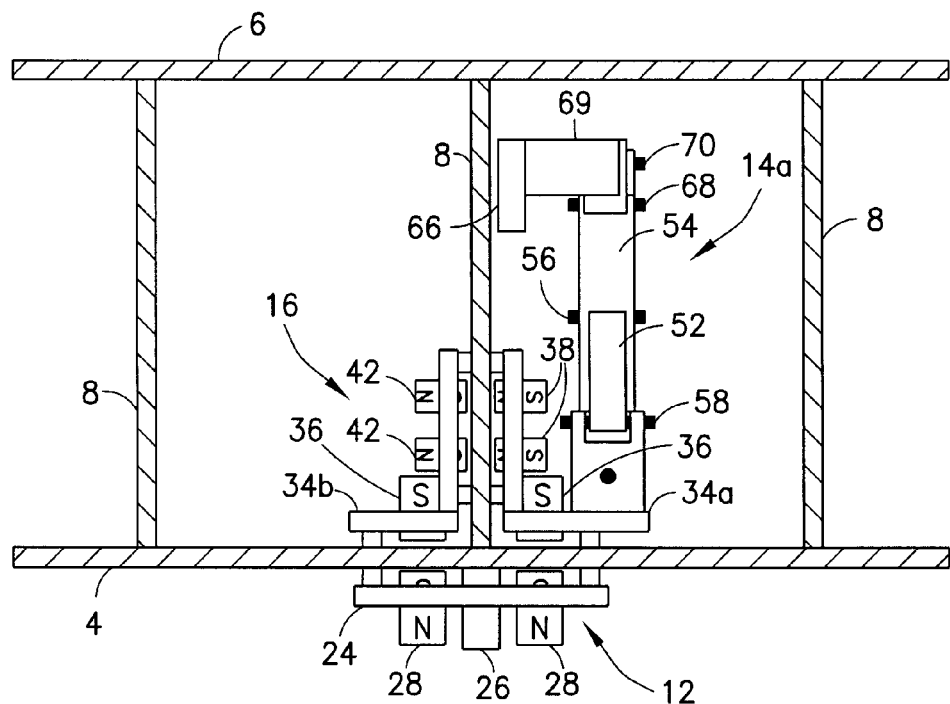
FIG. 9B is a diagram showing an end view of the tractor-trailer configuration depicted in FIG. 9A.

Referring to FIG. 9B, the scan arm frame 34a is secured in position by use of magnets 38 that couple through the spar web 8 to magnets 42 mounted to a passive trailer frame 34b. The through-web magnets 38 are embedded in a fixed position within the frame 34a of the arm scanner 14a and in association with the opposing magnets 42 embedded in the passive trailer frame 34b on the other side of the web 8. Magnets in the passive trailer component of some embodiments may be mounted on a slide mechanism (not shown in FIG. 9B) to accommodate ±15 degrees of vertical changes in the web. This relationship allows axial magnetic pole alignment and holds the scan arm frame 34a firmly against the web 8; it in turn holds the ultrasonic array probe into the web, thereby assuring reliable ultrasonic coupling.

In the configurations disclosed herein, the weight of the scan arm apparatus assists in helping the system to stay seated on the riding surface (flange) of the spar. The two chasses 34a,b are set into scanning motion in the X-direction by means of the drive tractor 12 which is magnetically coupled through the bottom skin 4 to the trailer chassis by means of respective sets of through-skin magnets (items 28 and 36 in FIG. 9B). In a direction normal to the web 8, the through-skin magnets 28 on the tractor 12 are separated from each other by a fixed distance. The through-skin magnets 36 on the scan arm frame 34a are embedded in trucks (not shown in FIG. 9B) that rotate relative to frame 34a about an axis parallel to web 8. In addition, the through-skin magnets 36 on the passive trailer frame 34b are also embedded in trucks (not shown in FIG. 9B) that rotate. These rotatable trucks, in turn, are slidably coupled to the passive vehicle frame 34b, which coupling allows the trucks to translate normal, or perpendicular, to the web. This ability to adjust the position of the trough-skin magnets on the passive vehicle in a direction normal to the web accommodates changes in cross web magnet spacing due to web thickness changes (0.10 to 0.50 inch) and web angle changes (±15 degrees). This sliding-rotating relationship allows axial magnetic pole alignment to be maintained between the truck magnets and the drive tractor magnets. The second benefit of the sliding truck magnets is that the tractor is allowed to follow the transitioning web in a manner similar to how a slot car would follow a track without any binding between the passive trailer chassis and the arm scanner chassis. (In another embodiment, for system configurations where gravity keeps the trailers firmly in contact with the bottom skin, if the X-direction motions of the spar arm scanner were self-powered (and the tractor vehicle were eliminated), then the trailer vehicles would not need through-skin magnets and means for adjusting their positions.)

More details concerning the structure and functionality of the spar arm scanner and its associated passive trailer vehicle can be found in U.S. patent application Ser. No. 13/470,125, the disclosure of which is incorporated by reference herein in its entirety.

Figure 10:
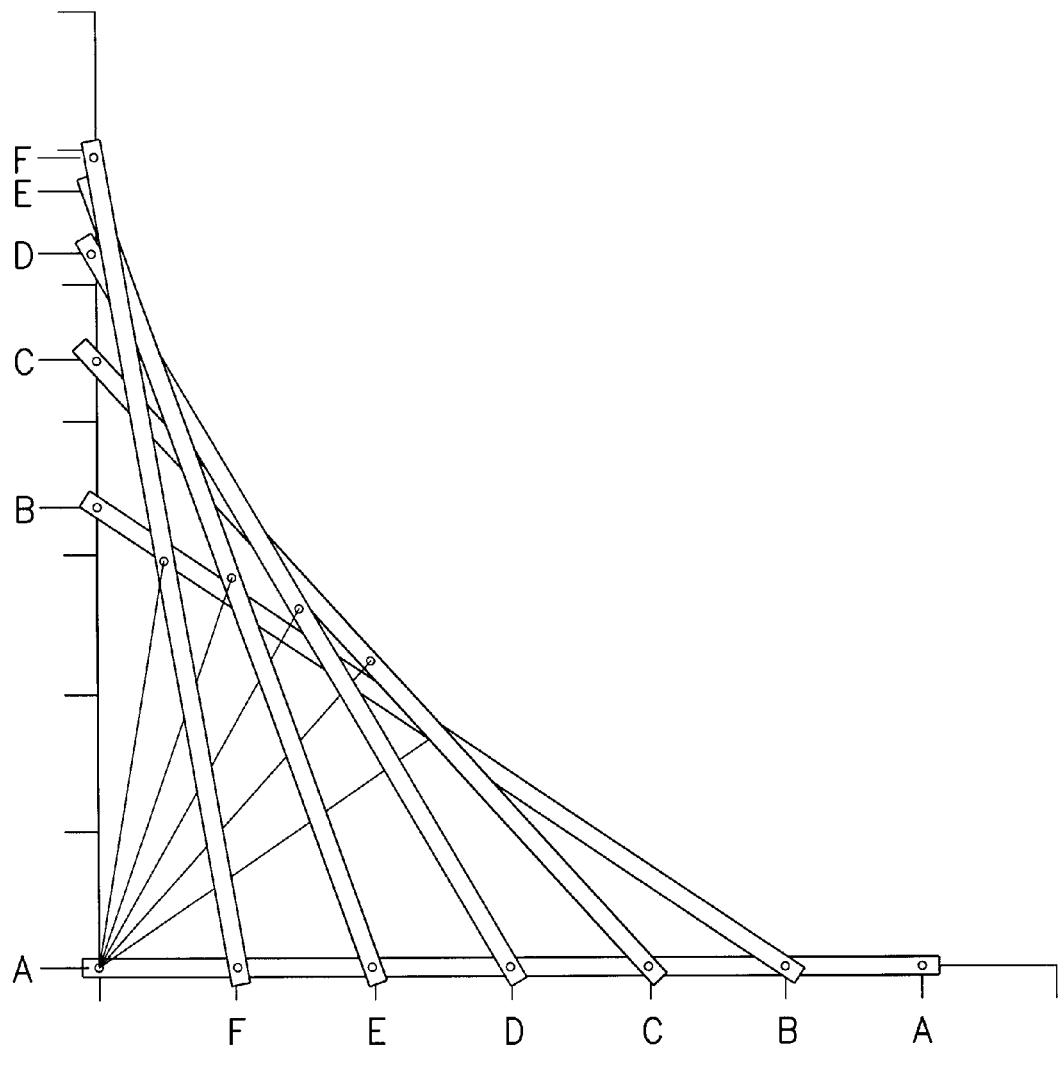
FIG. 10 is a diagram showing intermediate positions of the drive link (item 54) shown in FIG. 9.

FIG. 10 shows multiple intermediate positions of the drive link of the spar arm scanner as it is moved though its range of motion. The labeled positions (A, B, C, etc.) on the input end of the link, shown on the horizontal axis, correspond to the same labels for positions on the output (vertical) axis. Notice that the spacing on the input axis is uniform, but is non-uniform on the output axis. The vertical output position and vertical output velocity are nonlinear functions of the horizontal input position.

Since the output motion (position and velocity) of the lifting arm is not proportional to the input motion (i.e., non-linear), the control of the output position of the payload platform is not as simple as just counting the rotations of the lead screw and applying a scale factor. In order to move the payload to precise position a more complex control method is needed.

In order to control this mechanism, knowledge of the equations of motion of the mechanism can be used to develop a non-linear transfer function that describes the vertical position of the payload in terms of rotations of the lead screw throughout the entire range of motion. For this option, the stepper motor 46 and a lead screw rotary encoder (not shown in FIG. 9A) are far away from the water (and enclosed in housing for additional protection). This leaves the task of developing a process to convert lead screw rotations into vertical positions. To mathematically describe the relationship between the input and output motions, a non-linear transfer function needs to be developed. Not only must the vertical motion of the payload platform be described in terms of the lead screw rotations; the inverse function which describes lead screw rotations in terms of the vertical position of the payload platform is also needed. In robotics applications, defining the output Cartesian position in terms of an input actuator variable (position or rotation) is usually called forward kinematics, and defining the input actuator variable position or rotation in terms of the output Cartesian position is called inverse kinematics. The derivations of these functions are disclosed in U.S. patent application Ser. No. 13/470,125.

Figure 11:
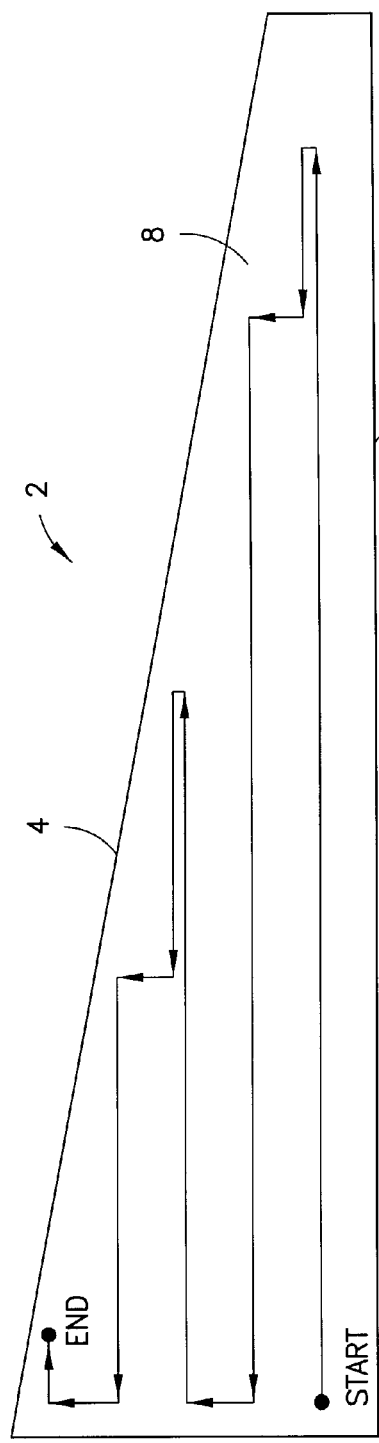
FIG. 11 is a diagram showing horizontal and vertical segments of motion path in accordance with one implementation.

Motion paths are loaded into the control software at runtime as a file that contains the individual horizontal and vertical motion segments (along with other calibration, velocity, and timing instructions). FIG. 11 shows an example motion path with multiple horizontal and vertical path segments. In this example, the motion path starts at the left end of the horizontal stabilizer tunnel produces a stair-step pattern that fits into the internal shape of the horizontal stabilizer. Smaller vertical steps may be programmed to get better coverage. Alternatively, the horizontal and vertical segments could be changed concurrently.

Figure 12:
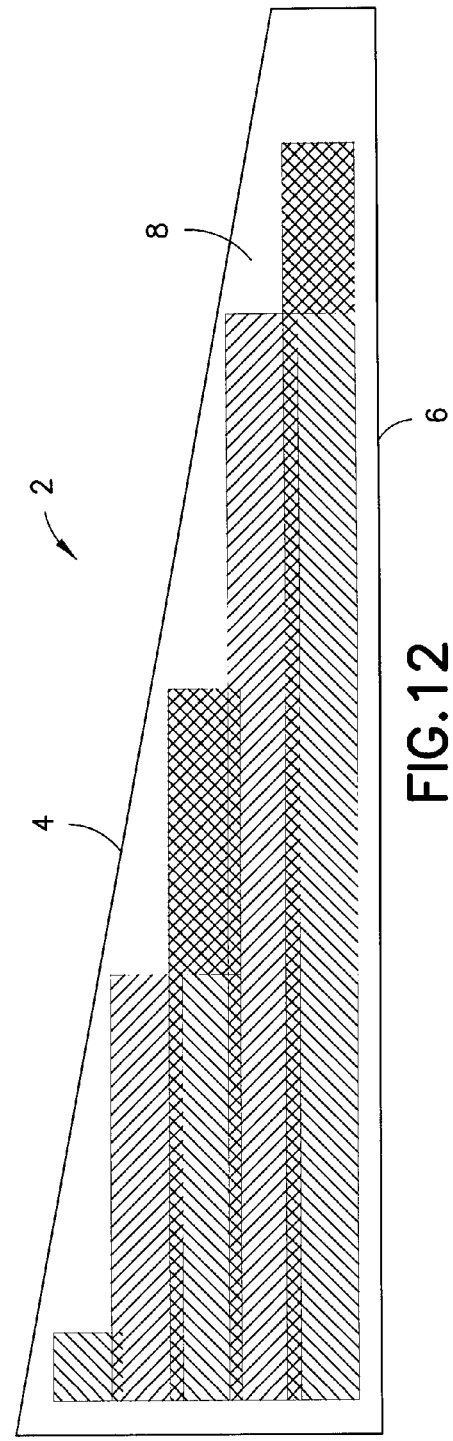
FIG. 12 is a diagram showing central spar web area scan coverage in accordance with one implementation.

FIG. 12 shows the resulting coverage area, where the cross-hatching lines "lean" in the direction of motion. Notice that there is some overlap in the coverage area. This is acceptable and even desirable in some areas to protect the overall motion plan against gaps in coverage. Overlap is handled properly by the scanning software application.

The above-described system positions the payload (NDI sensor) at specific locations while moving the payload at specified velocities. It also provides the horizontal and vertical positions of the payload to NDI scan software application running on a control computer. To achieve the foregoing, motion control and position measurement processes are implemented in software using available motor control interfaces and knowledge about the kinematics of the lifting arm.

To execute a motion path of the type depicted in FIG. 11, the spar arm scanner is placed at a starting position on the inboard end of the horizontal stabilizer and the tractor and other trailer vehicle are magnetically coupled to each other and to the spar arm scanner in the manner previously shown in FIG. 5. A motion plan is loaded into the control software application. After the vehicles are in position, a vertical height calibration is performed. After the flow of water has been turned on, the collection of data from the NDI sensor is started. The operator then signals the automated motion control process to begin. The motion control process then determines what type of motion path segment, horizontal or vertical, is called for by the loaded motion plan. If the next motion segment should be horizontal, the horizontal goal position is converted into a motor rotation count. The rotation rate and a start signal are then sent to the tractor drive motor. During motion in the X-direction, the motion control process determines whether the horizontal goal position has been reached. If not, then the speed is adjusted if necessary. If the horizontal goal position has been reached, the process determines whether additional motion path segments need to be executed. If not, then the motion control process terminates. If additional motion path segments need to be executed, the motion control process again determines what type of motion path segment, horizontal or vertical, is called for by the loaded motion plan. If the motion control process determines that the next motion segment should be horizontal, the sequence of steps described in this paragraph is repeated. If the motion control process determines that the next motion segment should be vertical, the target vertical position is converted into a lift motor rotation count using inverse kinematic equations. Then the rotation value and a start signal are sent to the lifting motor; and simulated encoder pulses are generated and sent to the NDI scanning system. During vertical motion, the motion control process determines whether the target vertical position has been reached. If it has, then motion control process again determines whether additional motion path segments need to be executed. If the target vertical position has not been reached, a warning is displayed on user interface and the actual vertical position of a specified point on the modified scissor linkage mechanism (e.g., a revolute joint axis) is computed. Corrected simulated encoder pulses are then sent to the scanning system. The motion control process then determines whether additional motion path segments need to be executed. The motion control process will repeatedly return to the step of determining what type of motion path segment is called for next by the loaded motion plan until a determination is made that there are no additional motion path segment. This enables the automated system to follow the loaded motion plan, such as the plan indicated in FIG. 11. The horizontal motion of the tractor vehicle and the vertical motion of the payload relative to the trailer vehicle can be controlled to provide the area scan coverage shown in FIG. 12 or other coverage schemes.

Spar Radius Scanner

In addition, the radii of each spar need to be inspected. For the purpose of illustration, a procedure will be described for inspecting a horizontal stabilizer having five spars, each with four radii, for a total of 20 radius inspections. The radius inspection apparatus is designed to work with the drive tractor on the top or bottom (i.e., the tractor is on the bottom of the top skin or on the top of the bottom respectively). There are two radius scanners (see left- and right-hand sweeping array radius scanners 14*b* and 14*c* in FIG. 18A), the only difference being that the connection cable exits from one end or the other. It is preferable for the cable to not be bent, which would be necessary if only one radius scanner were available. If needed, the cable can be bent, which means that either of the two radius scanners could be used to inspect all 20 radii. Each radius scanner is similar to the strip scanner in the way it is positioned and moved (i.e., each is a trailer vehicle pulled by the tractor). The radius scanner holds and positions the ultrasonic transducer array (i.e., sensor). A passive trailer on the other side of the spar (see trailer vehicle 16 in FIG. 4) is magnetically coupled across the spar web. The same tractor is placed on the top or on the bottom to move the sensor through the tunnel. The radius scanner comprises a linear ultrasonic transducer array that simultaneously sweeps and translates as it moves down the length of the tunnel. This sweeping linear array probe is described in detail in U.S. patent application Ser. No. 13/466,285, the disclosure of which is incorporated by reference herein in its entirety. The radius scanner is designed to adjust the position and orientation of the sensor so that its beam stays normal (or nearly normal) to a soft-tooled radius that varies in shape.

Each radius scanner is designed to provide a normal (i.e., perpendicular) sound entry and to inspect at a sufficiently fast rate. In the case of a linear ultrasonic array, the array is oriented lengthwise down the length of the radius and is mechanically pressed into the "as inspected" radius at 90 degrees so that sound entering the radius will enter normal to the front surface of the radius. It is then swept in the radial direction so that each part of the radius is inspected as the tractor/trailer system travels along the radius. The scanning mechanism is designed to keep the sensor normal to the front surface of the radius at all times. Simultaneous with the sweeping motion of the sensor, the radius scanner is translated down the length of the radius during movement of the tractor. The result is that the ultrasonic linear array, which is generally aligned with the radius, makes a simultaneous oscillating and translating motion that covers the entire radius with ultrasonic beams that are always normal (or nearly normal) to the surface at a high area coverage rate.

The motion control for the radius scanning system comprises three parts: the X-axis position control, the angular position control, and a synchronization process.

The X-axis motion (the X axis being parallel to the radius being inspected if the radius is linear) is provided by the tractor vehicle of the system, which uses data from a rotational encoder attached to an idler wheel on the radius scanner. The trailer component is pulled by the tractor and carries the scanner assembly. The X-motion drive motor and the sweeping motion drive motor are programmable stepper motors that can communicate with a personal computer through a serial communications interface. The operator or automated path planning system specifies the desired steady-state speed, direction, and an optional final goal position of the tractor-trailer system through a motion control software application. The X-axis positioning is controlled using proportional feedback of the encoder count data.

The process for controlling the sweeping motion (i.e., angular position) of the scanner assembly takes advantage of an on-board microprocessor in a stepper motor unit. A cyclic motion form is programmed into the motor, which takes cycle time, motion extents, and maximum acceleration data as the inputs. The system also uses a limit switch for calibrating the home angular position of the system.

When the X-direction motion of the tractor and the cyclic sweeping motion of the scanner assembly are used together, the resulting motion is a sawtooth path with rounded peaks and valleys (due to acceleration/deceleration). When operated at the appropriate speed, a continuous area scan will be created.

If the X-direction motion of the tractor is too fast, gaps will appear in the scan data. To address this issue a process has been developed to synchronize the X-direction velocity of the tractor with the motion of the oscillating sensor mechanism. This process uses the cycle rate, angular motion range, and sensor width to compute the appropriate tractor velocity. The process also has a scaling variable to ensure that there is a small amount of overlap to compensate for minor fluctuations in velocity as the system moves (such as velocity disturbances transmitted by the tractor-trailer coupling system).

Once the fixed parameters of sensor width, angular motion range and overlap are set, the entire process can be controlled by a single variable—the cycle rate. This will compute and set the X-direction velocity of the tractor to provide full scan area coverage without gaps in the data.

Figure 13A:
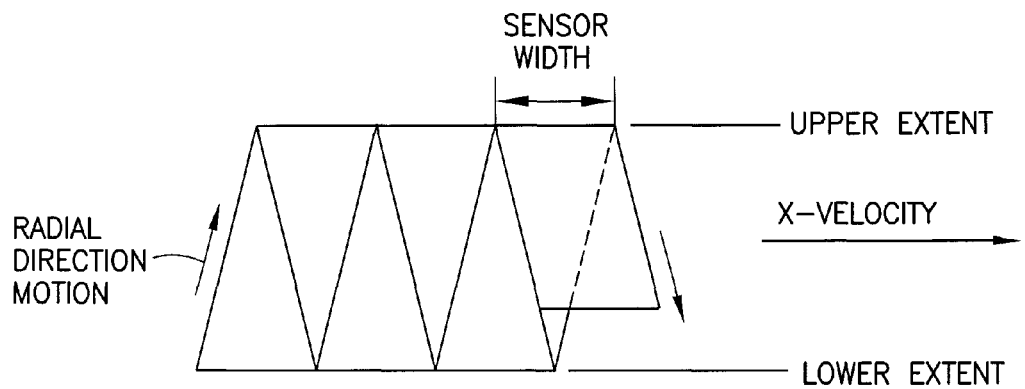
FIGS. 13A through 13C are diagrams showing different radius scan patterns: (A) exact coverage pattern; (B) X velocity too large (or cycle rate too slow); and (C) pattern with a small amount of overlap.
Figure 13B:
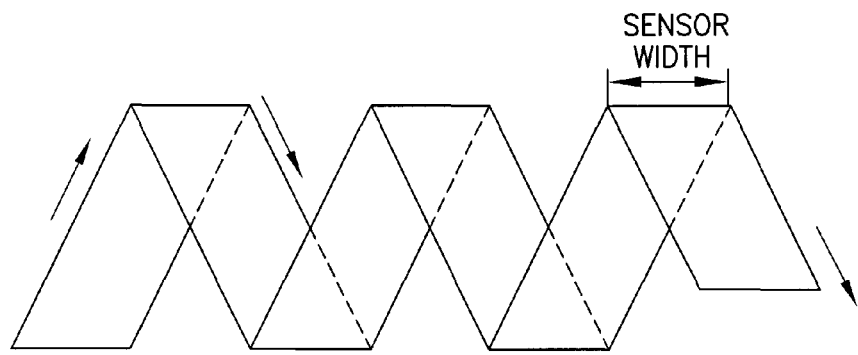
Figure 13C:
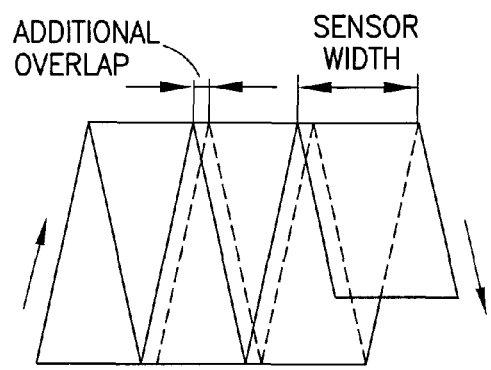

FIGS. 13A through 13C illustrate the different aspects of this motion synchronization, showing three potential coverage patterns. FIG. 13A shows the exact coverage pattern with no overlap and no gaps, but this pattern could produce gaps if the X-direction speed were to fluctuate. FIG. 13B shows the pattern when the X-velocity is too high, or equivalently if the cycle rate is too slow. FIG. 13C shows the pattern with a small amount of overlap. The overlap ensures coverage when the X-direction speed fluctuates by less than a specified amount, the amount of overlap needed being a function of the maximum fluctuation to be expected.

Figure 14:
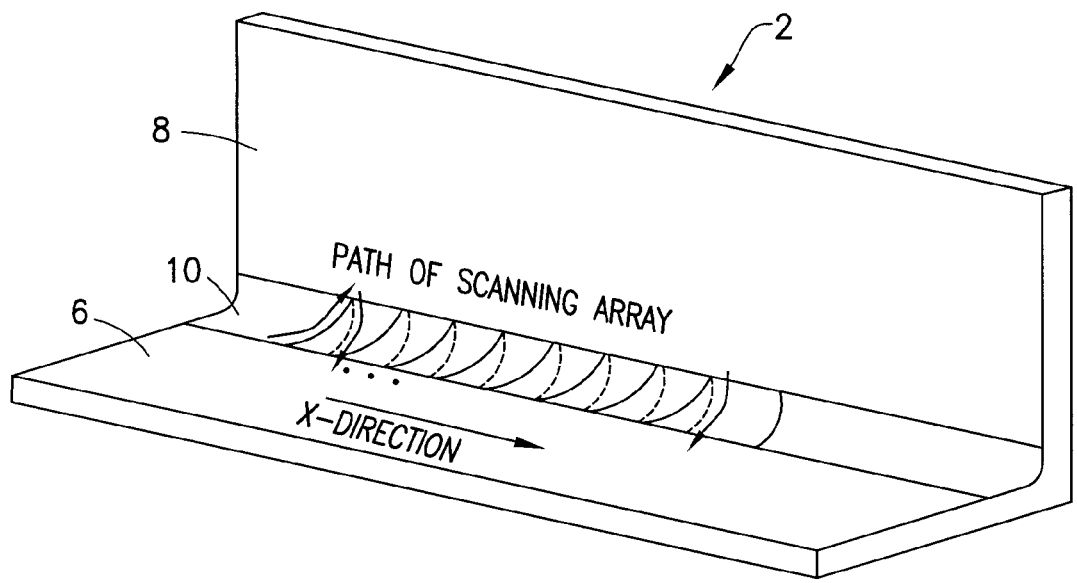
FIG. 14 is a diagram showing an isometric view of a portion of a horizontal stabilizer with a radius scan pattern imposed thereon. The solid and dashed curved lines respectively represent alternating upward and downward scans as the scanner travels along the length of the radius.

FIG. 14 is a diagram showing an isometric view of a portion of a horizontal stabilizer with a radius scan pattern (of the type shown in FIG. 13A) imposed thereon. The solid and dashed curved lines respectively represent alternating upward and downward scans as the radius scanner travels at a constant speed along the length of the radius (i.e., in the X-direction).

Besides the unique motion of the ultrasonic array, an important part of solving the problem of a non-uniform "radius" is ensuring that the sound enters the part at or nearly at 90 degrees or normal to the front surface. It is important to keep the direction of ultrasound entry normal to the radius front surface during the entire sweep of the radius. If the radius were truly circular, that would be trivial. The radius that is obtained from soft-tooled parts, whether they are designed to be constant or to vary by part location, will, due to the nature of radii obtained by soft-tooled fabrication techniques, "vary by manufacturing". As this is not an actual circular radius but rather a spline curve that can vary over different areas of the part or from part to part even though the design is for a constant radius in all areas, it represents a difficult and unique mechanical challenge to design and build an apparatus that can maintain sensor-to-part surface normality over the entire sweep of the radial motion and over a not-known-in-advance variety of "radial" shapes. In accordance with one embodiment, the ability to maintain normality over an unknown "radius" is provided using the mechanical design described hereinafter.

Figure 15:
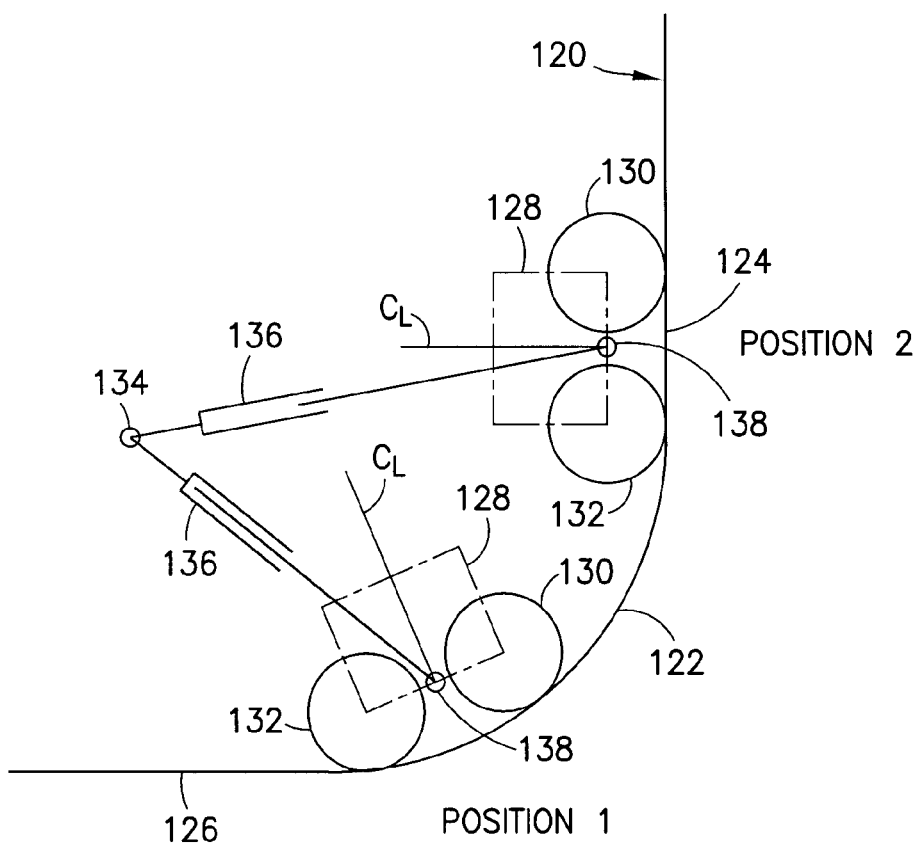
FIG. 15 is a schematic representation of a combined sweeping and toppling motion of a sensor in accordance with one embodiment that seeks to maintain a centerline of the sensor normal or near normal to the inspected surface.

FIG. 15 illustrates a cross section of a surface 120 of a part comprising a circular fillet 122 between two flanges 124 and 126. It also shows components of a rotating subassembly that is supported by a non-rotating subassembly of a radius scanner. The rotating subassembly comprises a fixture 128 (referred to hereinafter as a "toppler") that holds the sensor (not shown) perpendicular to a centerline CL between two surface followers 130 and 132. These followers 130, 132 may be rolling wheels of various shapes, or solid rubbing blocks, depending upon the requirements of the particular part being inspected and the required duration of the inspection. Note that as this sort of assembly is swept along the surface, the centerline CL through the sensor remains normal to the local surface 120 between the followers 130, 132. It should be noted that the spacing between the two followers should be selected according to the expected degree of surface variability. In other words, a surface whose curvature changes rapidly needs followers that are closer together.

Some means for sweeping around the inspected range of travel must be provided, and one method is illustrated in FIG. 15. A fixed position pivot 134, called the "sweep pivot", is held at some location in space relative to the part surface 120, by means of one of any number of different types of carriage mechanisms (such mechanisms are well known). A telescoping pressure slide 136, swept through a range of angles, is used to push the toppler 128 against the surface 120 of the part, by means of a topple pivot 138 placed as near to the surface 120 as possible so as to minimize the tendency of the toppler 128 to "topple" if it encounters an obstruction during the sweep. The slide 136 may telescope toward the surface 120 due to forces exerted by springs, hydraulic or pneumatic actuators, or other means for applying force along a direction. Pivot 134 is driven by a motor (not shown) in an oscillating pattern to produce sweep coverage of the fillet 122, plus a small amount of the flat surfaces 124 and 126 near fillet 122.

In accordance with one embodiment, the radius scanning system comprising a support assembly, a sweeper assembly pivotably coupled to the support assembly for pivoting about a sweep axis (i.e., the axis of sweep pivot 134 in FIG. 15), and a sensor carried by the sweeper assembly. The sweeper assembly in turn comprises a sensor position adjustment subassembly (comprising toppler 128 in FIG. 15) that allows the sensor to move in a direction normal or nearly normal to the sweep axis and orient so that its centerline is normal or nearly normal to the surface being inspected. The adjustment of the sensor orientation is enabled by the toppler, which is pivotable about a topple axis (i.e., the axis of topple pivot 138 in FIG. 15). One embodiment of such a system is described inn detail in U.S. patent application Ser. No. 13/466,285.

In accordance with an alternative embodiment, instead of mounting a sweeping array on a radius scanner platform, the radius scanner may comprise one or more phased arrays that produce steered beams at different angles.

Each of the different scanners described above is used at a different stage in the overall inspection process. Each scanner is used in conjunction with a respective passive trailer vehicle that is placed on the other side of the spar, each such passive trailer vehicle being designed to magnetically couple to a corresponding one of the scanners. In one implementation, the same tractor vehicle is used to move the respective sets of scanners and passive trailer vehicles along the length of the spar.

Computer System and Software

Regardless of which scanner is being used, the tractor, scanner, and other system components are controlled by a computer system in response to commands input via a graphical user interface by the system operator or through an automated process using pre-planned motion instructions to control the system. The motors onboard the radius scanner, the arm scanner and the trailer are connected to an electronic control box by means of flexible electrical cables. The electronic control box contains the system power supplies and integrates all the scanner control connections and provides an interface between the computer and the scanners and tractor.

The computer system may comprise a ground-based computer that hosts motion control application software and NDI scan application software and is connected to at least one video display monitor. The motion control application software controls the various motors onboard the tractor and trailer vehicles, the cable management sub-system, the couplant water valve, and the indicator display lights; the NDI scan application software controls ultrasonic data acquisition and display. Optionally, an additional monitor may be provided for displaying live video from a camera mounted on a scanner or other data. A person skilled in the art will recognize that multiple computers or processors could be used, for example, to separately execute the motion control and scanning functions.

Motion Control Software

The computer hosts the motion control and scanner control software. The motion control software is a centralized controller that provides manual and automatic interaction with the motors, position sensors, and indicators that are used to move the payload (NDI sensor) at specified speeds to specified locations.

The motion control software simultaneously controls the actions of multiple moving and non-moving components, which include: a motion drive unit (i.e., the tractor), a variety of sensor payload units (i.e., the active trailer vehicles), a cable handling system, the water supply system, and indicator/warning beacons.

Each one of these components contains some type of controllable motor, actuator, sensor, or display element that can be read or written to through the system's interface hardware. Since the system can be configured in various ways using the tractor drive unit with different active trailers, the software also controls a relay module that connects or disconnects the signal and power lines to these various components.

A control command library provides methods that can be issued through interactive or automated (scripted) control to communicate with the various components. These commands allow high-level access to data measured by positioning sensors (such as the wheel encoders), motion control variables (such as drive speed, desired position, solenoid valves on/off), and display items (such as indicator lights). The commands include single events, such as turning on a relay, and also more complex commands that comprise a series of actions, such as position feedback control to move the tractor or arm to an exact position, or to synchronize the oscillating speed of the radius scanning motor with the drive speed of the tractor.

This command library can be used in an on-line, manual control mode though direct user commands that can be entered as text, through a graphical user interface, or other input device, such as a wireless remote control unit or gamepad (joystick) interface. The command library can also be used in an automated form in which a sequence of commands defined in an instruction or "script" file are read into memory and executed in the desired sequence by the controller.

The motion control application consists of two major elements: the motion control module and the graphical user interface. These elements can be combined into a single application or be separate applications that are connected through a data connection, such as network sockets. When they are separate elements, it is possible to configure the system to allow the motion control module to be run on one computer and the graphical interface to be run on another computer. This configuration allows remote operation of the system.

At the lower level, the software interfaces with the various components through USB/serial (RS-422 or RS-232) connections. This includes: (1) the USB interface to a data acquisition device, which reads encoders, digital inputs, etc.; (2) serial port interfaces to the various stepper motors used on the tractor, trailers, and cable handling system; and (3) the serial port interface to the relay control module. These low-level controls are available to the user through the command library for manual or automated (scripted) control.

Figure 16A:
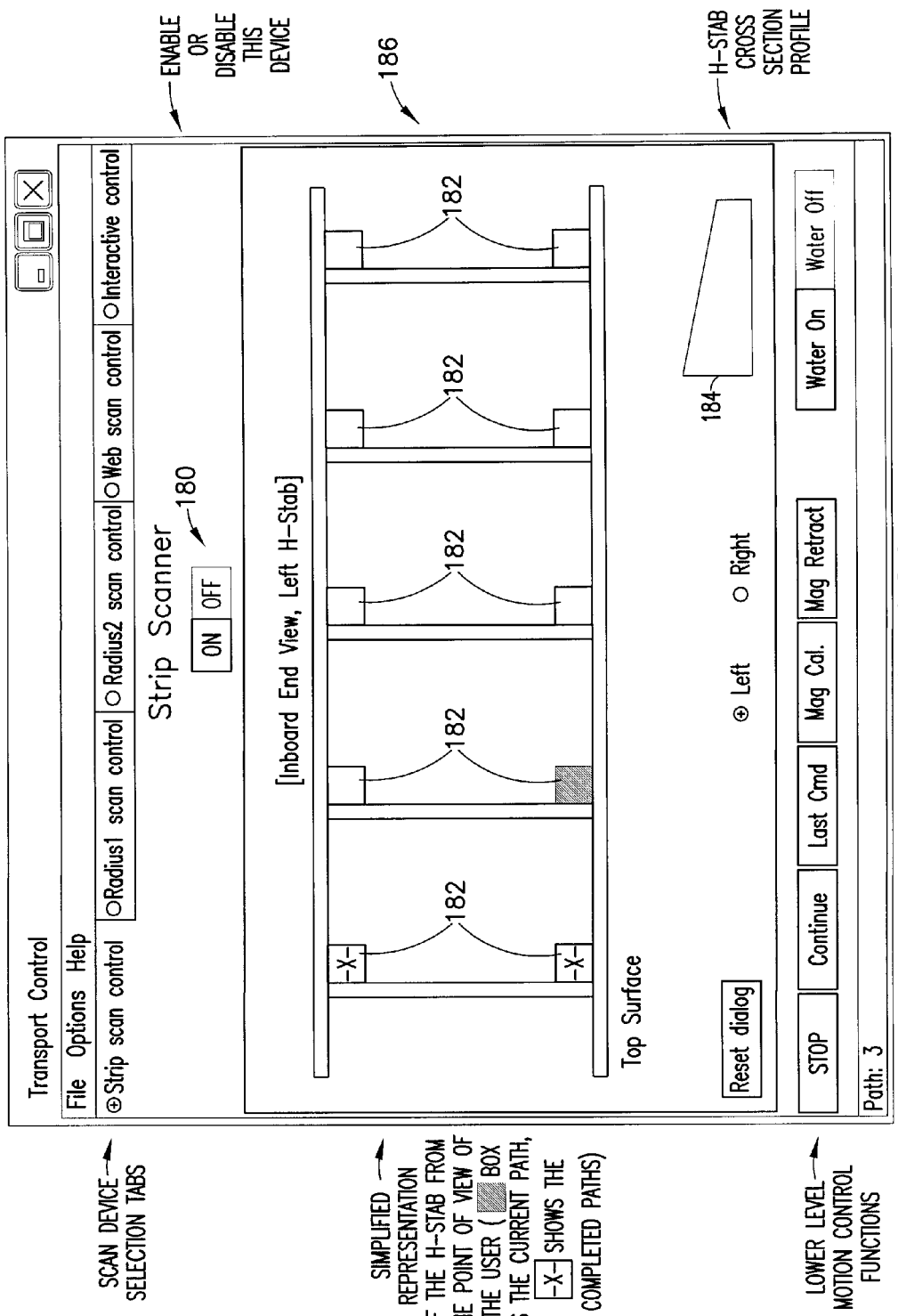
FIGS. 16A through 16D are diagrams representing various screen shots of a graphical user interface for controlling the inspection system disclosed herein.
Figure 16B:
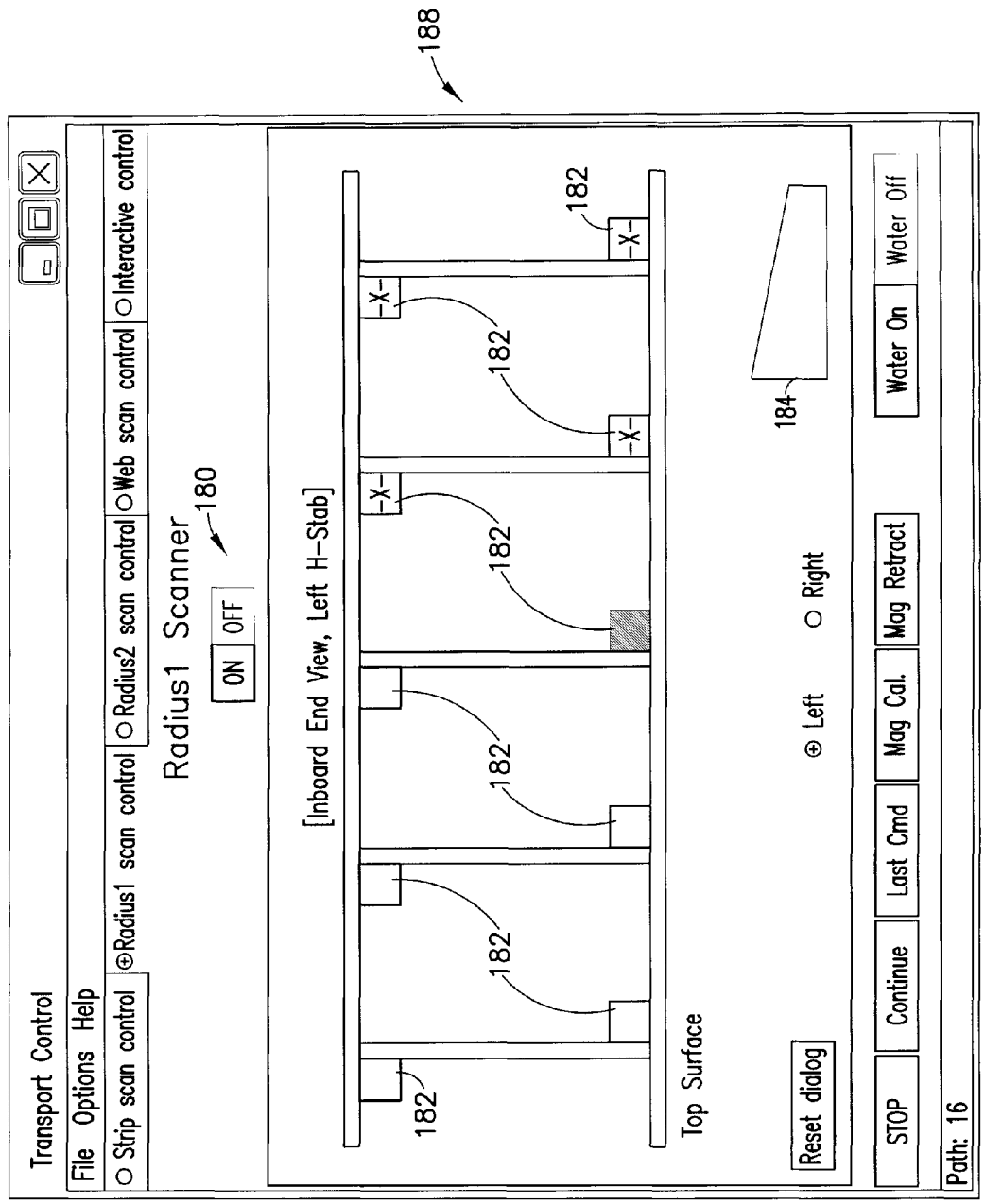
Figure 16C:
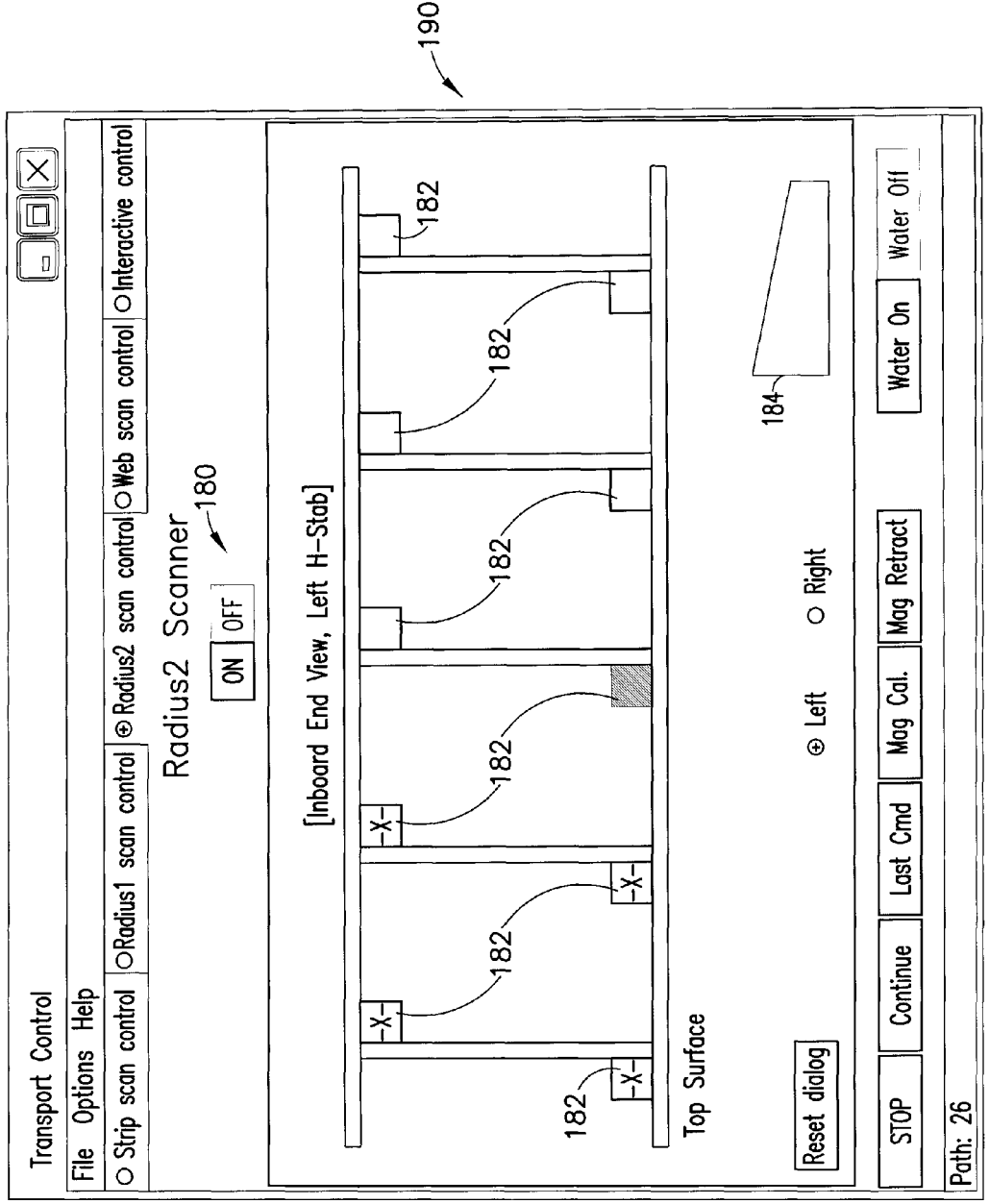
Figure 16D:
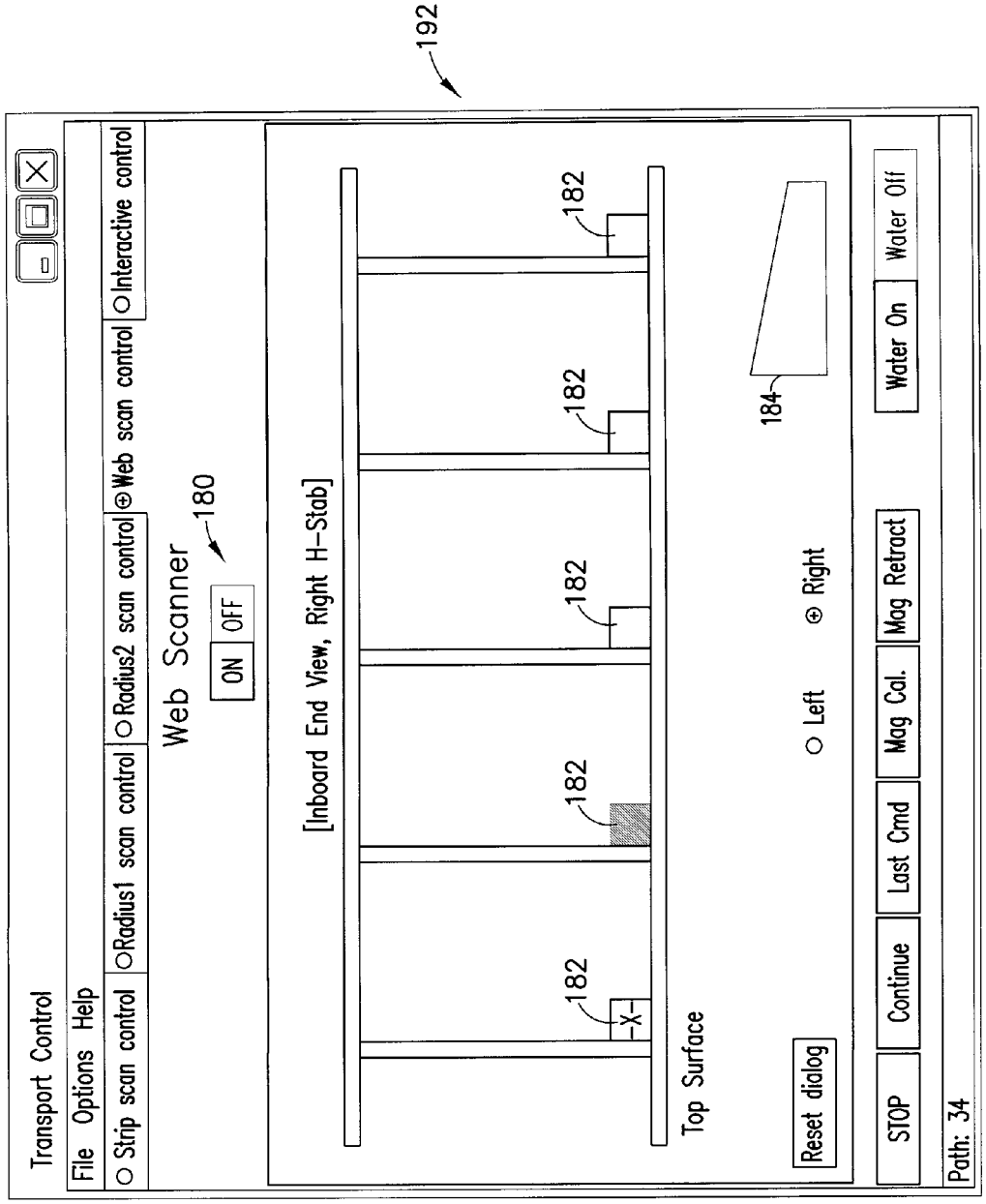

At the high level, the user can interact with the application through a graphical user interface. Four screen shots of a graphical user interface in accordance with one embodiment are respectively shown in FIGS. 16A-16D. The graphical user interface comprises multiple interaction "tabs", which separate the control commands for each type of scanner. Window 186 (FIG. 16A) can be used to control the edge scanning equipment; windows 188 (FIG. 16B) and 190 (FIG. 16C) can be used to control radius scanning equipment having respective left- and right-hand radius scanners; and window 192 can be used to control the central web scanning equipment (FIG. 16D). Each window has ON/OFF virtual buttons 180 for enabling or disabling the respective scanning devices.

Each screen shot shown in FIGS. 16A-16D displays a two-dimensional visual representation of the target object to be scanned, which in this case is the inboard end of the horizontal stabilizer. Layered over the two-dimensional target object representation are a series of virtual buttons 182 that represent the individual motion paths that can be selected and executed. Internally these buttons are associated with specific motion script files that contain the parameters associated with that specific path. The buttons 182, which can be used to select the active motion path, are positioned in a way that they correspond to the actual position of the scanning devices on the part being scanned from the operator's point of view. This one-to-one correspondence makes it easier to keep track of which motion path sequence will be used, as well as marking (with an "-X-") which scans have been completed. The current motion path is indicated by a shaded button 182 in each of FIGS. 16A-16D. The empty buttons 182 indicate which scan have not been completed yet. This symbology helps the operator keep track of the current scan path, the areas that have been scanned, and the areas that still need to be scanned. This user interface gives a simple visual representation that is easy to use and can be operated with little additional training.

The interface also gives the user choices for other options, such as selecting either the horizontal stabilizer for the left side of the airplane or for the right side (see the radio buttons respectively labeled "Left" and "Right" in each of FIGS. 16A-16D). The trapezoid 184 in each of FIGS. 16A-16D represents the actual shape of the part as seen from the operator's location. The left- and right-side horizontal stabilizers look different, so this element helps the operator confirm that he/she has the proper side selected.

Each window shown in FIGS. 16A-16D further comprises a set of virtual buttons for actuating various motion control functions. In response to the operator clicking on a respective button, the following respective functions are performed: STOP—stops all motion; Continue—the function that proceeds with the path script file until it reaches a hold/wait statement; Last Cmd—re-issues the last command sent to the motor control; Mag Cal.—performs a magnet calibration and home sequence on the tractor magnets; Mag Retract—retracts the tractor magnets; Water On—the supply of water to the scanner is turned on; and Water Off—the supply of water to the scanner is turned off. These same commands are also available on a handheld wireless remote device (i.e., wireless jog pendant 270 in FIG. 18B) that the operator can carry while working at the inspection site.

Scan Sequencing

Figures 17, 17A, 17B:
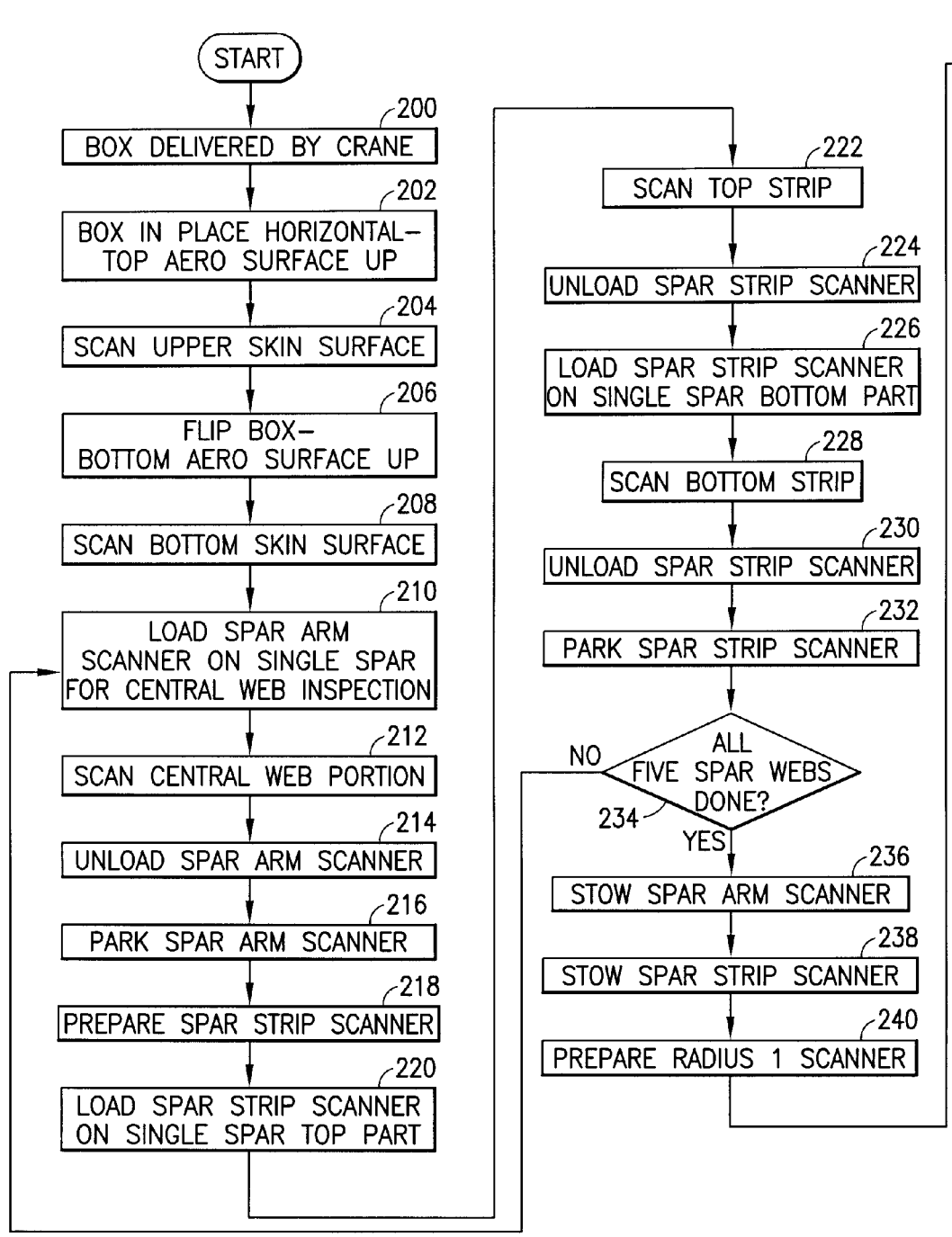
FIG. 17 is a flowchart (presented in two parts A and B) showing the sequencing of applying the various ultrasonic scanners to perform a complete interior nondestructive inspection of a hollow composite structure in accordance with one implementation.
Figure 17B:
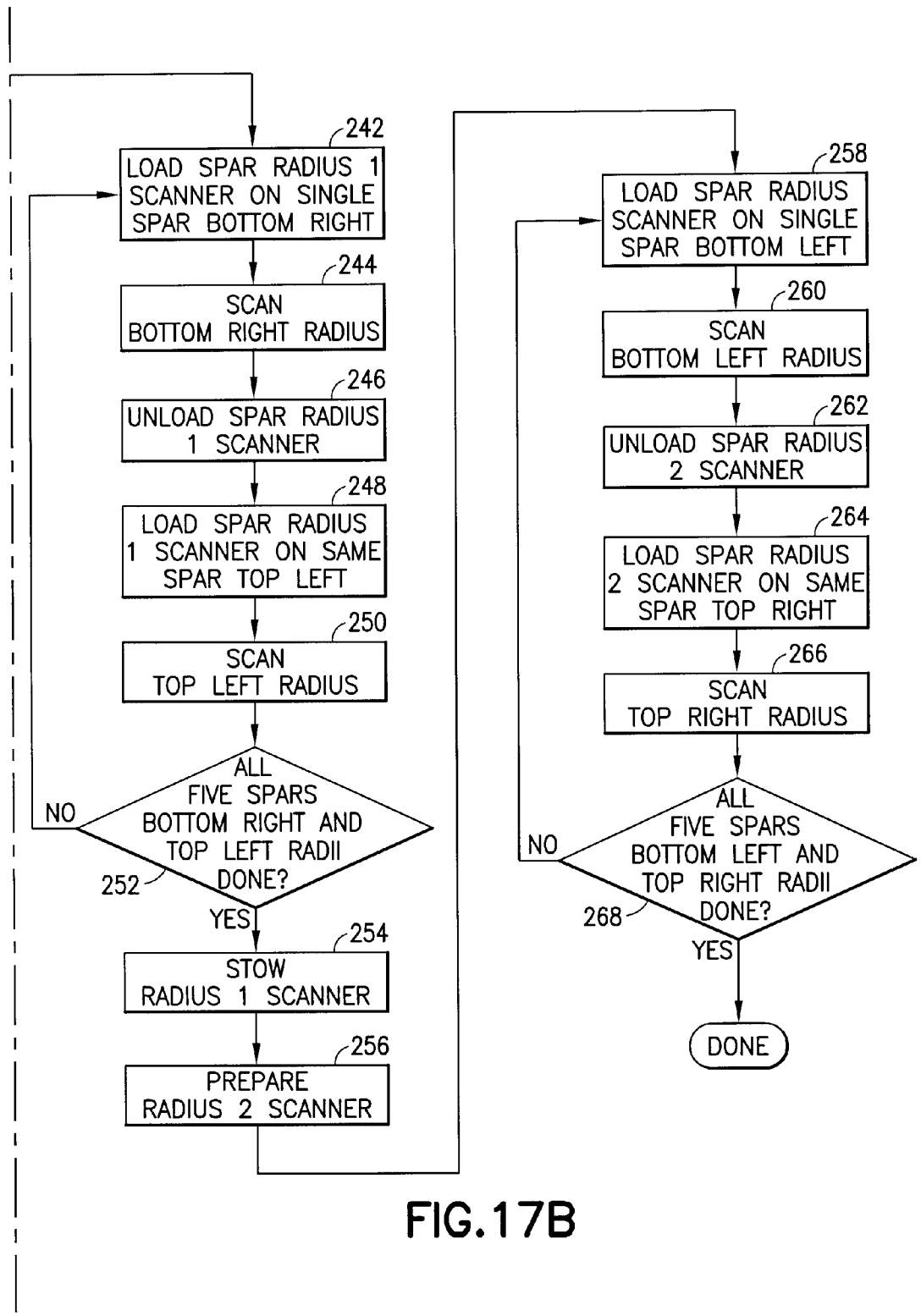

A further aspect of the NDI system disclosed herein is the sequence of applying the various ultrasonic scanners to do a complete interior inspection. All of the interior and even the exterior skin inspection are done using pulse echo ultrasonics. For example, the echo returned from the back surface of the structure being inspected can be monitored. Any flaws in the structure can disrupt the sound reaching and reflecting from the back surface and will show up on the ultrasonic scans as indications that need investigation and disposition. To get a clean back surface echo, there needs to be a dry back surface. Water drops on the back surface can show up as indications on the ultrasonic scans. As each channel of the horizontal stabilizer requires a complete inspection with water wetting most of the surfaces, the sequence of inspections can be selected to prevent any inspection being done on a surface whose back surface has been exposed to water during a previous inspection. FIG. 17 (comprising parts A and B) shows a sequence that has been developed for inspection of a horizontal stabilizer, which sequence avoids water on the back surface of an area being inspected. First all the external skins are inspected. Then all the spar webs are inspected, with the sequence always starting on an outside surface of an outside spar. This ensures that any water splash does not reach the back surface of an area that has not previously been inspected. Last, the radii are inspected as this inspection does not rely on a back surface ultrasonic echo.

As used in FIGS. 17A and 17B, the term "unload" means to take a scanner off the horizontal stabilizer; the term "park" means to put the scanner somewhere it can be easily put back on the part (e.g., on a holding shelf/table); and "stow" means to put the scanner away (e.g., inside a drawer in a storage cabinet).

Referring to FIG. 17A, the operation begins by delivering a horizontal stabilizer (i.e., "box") to the inspection site by crane (step 200). The horizontal stabilizer is placed on the part holding tools with its top aerodynamic surface facing up (step 202). Then the upper skin surface of the horizontal stabilizer is scanned (step 204). The horizontal stabilizer is then flipped over so that the bottom aerodynamic surface is facing up (step 206). Then the bottom skin surface is scanned (step 208). Top and bottom skin surfaces are inspected from the exterior using convention NDI techniques. Upon completion of the scan of the bottom skin, the spar arm scanner is loaded on a single spar for central web inspection (step 210), which is magnetically coupled to the drive tractor on the opposite side of the skin surface. (For the remainder of the discussion of FIG. 17, it will be assumed that the tractor is always installed on the opposite side of the skin surface when any of the scanner devices is loaded onto the horizontal stabilizer.) The central web portion of the selected spar is then scanned (step 212) in the manner shown in FIG. 12. Upon completion of step 212, the spar arm scanner is unloaded (step 214) and then parked (step 216). The spar strip scanner is prepared (step 218) and then loaded on a top part (e.g., strip B1 in FIG. 7) of the selected spar (step 220). The top strip is then scanned (step 222). The spar strip scanner is unloaded from the top part (step 224) and then loaded on the bottom part (e.g., strip B2 in FIG. 7) of the selected spar (step 226). The bottom strip is then scanned (step 228). Upon completion of step 228, the spar strip scanner is unloaded (step 230) and then parked (step 232). By monitoring inputs from the strip and web scan control tabs of the user interface, the motion control software application running on the control computer then determines whether all spar webs of the horizontal stabilizer have been scanned (step 234). If not, then the process returns to step 210, i.e., the spar arm scanner is loaded onto the next spar to be inspected. If the control computer determines in step 234 that all spar webs have been scanned, both the spar arm scanner and the spar strip scanner are stowed (steps 236 and 238) and the first radius scanner is prepared (step 240).

Referring to FIG. 17B, the process continues by loading the first radius scanner on the bottom right of a selected spar (step 242). The radius on the bottom right of the selected spar is then scanned (step 244) in the manner shown in FIG. 14. The first radius scanner is unloaded from the bottom right (step 246) and then loaded on the top left (step 248) of the selected spar. The radius on the top left of the selected spar is then scanned (step 250). By monitoring inputs from the first radius scan control user interface, the motion control software application running on the control computer then determines whether the bottom right and top left radii for all spar webs of the horizontal stabilizer have been scanned (step 252). If not, then the process returns to step 242, i.e., the first radius scanner is loaded onto the next bottom right radius to be inspected. If the control computer determines in step 252 that the bottom right and top left radii for all spar webs have been scanned, the first radius scanner is stowed (step 254) and the second radius scanner is prepared (step 256). The second radius scanner is then loaded on the bottom left of a selected spar (step 258). The radius on the bottom left of the selected spar is then scanned (step 260). Next, the second radius scanner is unloaded from the bottom left (step 262) and then loaded on the top right (step 264) of the selected spar. The radius on the top right of the selected spar is then scanned (step 266). By monitoring inputs from the second radius scan control user interface, the motion control software application running on the control computer then determines whether the bottom left and top right radii for all spar webs of the horizontal stabilizer have been scanned (step 268). If not, then the process returns to step 258, i.e., the second radius scanner is loaded onto the next bottom left radius to be inspected. If the control computer determines in step 268 that the bottom left and top right radii for all spar webs have been scanned, the inspection is complete.

Figure 18B:
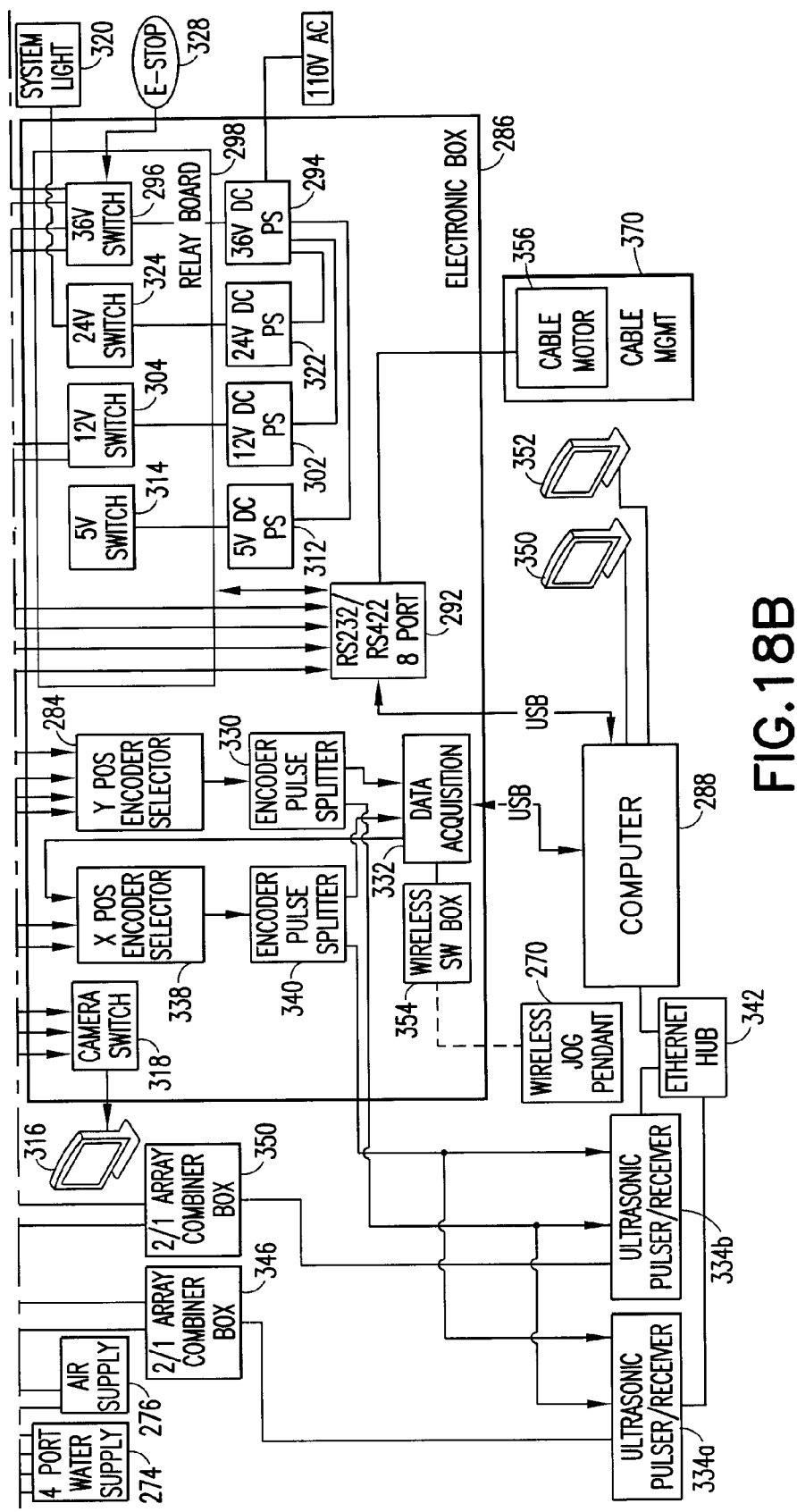
FIG. 18 is a schematic (presented in two parts A and B) showing components of a system for performing a complete interior nondestructive inspection of a hollow composite structure in accordance with one embodiment.

One implementation of the above-described NDI scanning system is depicted in FIG. 18, which comprises parts A and B. FIG. 18A shows selected components of the following vehicles: a tractor 12, a spar arm scanner 14*a*, a left-hand sweeping array radius scanner 14*b*, a right-hand sweeping array radius scanner 14*c*, and a spar strip scanner 14*d*. Each of these vehicles is connected to the system components shown in FIG. 18B by means of a respective flexible cable. The cables are guided by the cable management system disclosed herein. The cable connections between the components in FIG. 18A and the components in FIG. 18B include electrical power, data and control lines, water lines and air supply lines, as described in more detail below.

Each of scanners 14*a*-14*d* has a respective array water chamber 272 (see FIG. 18A) which is connected by a respective water line to a four-port water supply system 274 (see FIG. 18B), each port being opened and closed by manual operation of a respective water control valve. (Alternatively, it would be possible to control the state of the individual water valves by computer.) Motion control software running on the computer 288 controls the water going into the four port water supply system in response to operator inputs (i.e. water on or water off) The valve controlling which of the four ports is active is hand switched by the operator. Only the water supply port corresponding to the scanner being used will be open; the other three ports will remain closed during operation of one scanner.

In addition, the respective housings or drive modules for scanner motors 278 of radius scanners 14*b* and 14*c* (see FIG. 18A) receive pressurized air from an air supply 276 (see FIG. 18B) via a respective air line (which pressurized air inside keeps water out of the drive module).

Referring to FIGS. 18A and 18B, the drive motor 290 and two magnet motors 306 on tractor 12 and the scanner motor 278 on whichever scanner 14*a*-14*c* is in use each receive power from a 36-volt DC power supply 294 via respective power lines in response to closure of a switch 296 that is part of a relay board 298. The 36-volt DC power supply 294 receives power from an uninterruptible power supply 326. The closure of switch 296 is activated by a signal received from computer 288 via a serial (RS-422 or RS-232) port interface 292. The system operator can open switch 296 in an emergency by pressing E-stop button 328.

The computer 288 may comprise a general-purpose computer programmed with motion control application software comprising respective software modules for controlling the various stepper motors on the tractor 12 and scanners 14*a*-14*c*. The computer 288 outputs control signals to scanner motors 278, tractor drive motor 290, magnet motors 306 and cable motor 356 via serial (RS-422 or RS-232) port interface 292 to selectively activate/deactivate each motor. When activated, the stepper motors are programmed to execute respective motion control functions in accordance with selections made by the system operator using an interactive control interface (not shown).

Commercially available stepper motors have existing position and velocity control modes, but neither of these modes is perfectly suited for the type of control needed for horizontal position control in the above-described application. In the motor manufacturer's existing interface, the velocity mode by itself does not allow precise positioning, and the control of velocity in the position mode is limited and does not allow the level of adjustment during motion sequences that is needed. So a hybrid solution for horizontal control was developed using the motor velocity mode and information from an external encoder.

The horizontal motion control objective for this system is to move the magnetically coupled vehicles at a constant velocity (rate) and come to a stop at a specified goal position. In a horizontal motion control process in accordance with one implementation, the motor manufacturer's velocity control mode is supplied in the low-level motion control firmware by setting the desired velocity, while a separate proportional-integral-derivative (PID) closed-loop feedback process using data from the external encoder is included by the high-level motion control software to modify the velocity at run-time to make sure that the trailer vehicle comes to a stop at the desired location. The process is implemented using an encoder that measures the rotation of a surface contact wheel (item 72 in FIG. 9A) that is rotatably coupled to the frame of the scanner.

Referring to FIG. 18B, the computer 288 also hosts ultrasonic data acquisition and display software that controls a pair of ultrasonic pulser/receivers 334*a* and 334*b*. Optionally, a single pulser/receiver unit or more than two pulser/receiver units can be used. Computer 288 communicates with the pulser/receivers 334*a,b* via an Ethernet hub 342. In one implementation, the ultrasonic pulser/receiver 334*a* is coupled to either web strip array 344 of the spar strip scanner 14*d* or web array 348 of the spar arm scanner 14*a* (see FIG. 18A) by means of a first 2/1 array combiner box 346 (see FIG. 18B); while the ultrasonic pulser/receiver 334*b* is coupled to either radius array 280*a* of the first radius scanner 14*b* or radius array 280*b* of the second radius scanner 14*c* (see FIG. 18A) by means of a second 2/1 array combiner box 350 (see FIG. 18B). The ultrasonic pulser/receivers 334*a,b* send pulses to and receives return signals from the respective linear ultrasonic transducer arrays via the respective combiner boxes. Each array has 64 elements; the combiner boxes allow standard 128-element cables to be utilized. The NDI scan application software running on computer 288 controls all details of the scan data and the display of data. The pulser/receivers correlate the acquired ultrasonic data with position information received from a data acquisition device 332, as will be described in more detail below.

Referring to FIG. 18B, the computer 288 is connected to a pair of display monitors 350 and 352, one of which displays the graphical user interface shown in FIGS. 16A-16D. Optionally, only one display monitor can be used. As previously mentioned, some of the commands available on the graphical user interface are also available on the wireless jog pendant 270, which communicates with the data acquisition device 332 via a wireless switch box 354 incorporated in the electronic box 286. The states of the switches on relay board 298 are controlled by computer 288 via the RS232/RS422 serial interface 292 (indicated by a single double-headed arrow in FIG. 18B; individual connections between serial interface 292 and the relay board switches are not shown to avoid clutter).

Each of scanners 14*a*-14*c* may be equipped with a camera 300 (see FIG. 18A) that captures a live view of the scan head mechanism. When a camera-equipped scanner is selected for use, the respective camera 300 on the selected scanner receives power from a 12-volt DC power supply 302 (see FIG. 18B) via a respective power line in response to activation of a switch 304 that is part of relay board 298. Switch 304 is activated by computer 288 via serial (RS-422 or RS-232) port interface 292. Video from an active camera 300 is received by a display monitor 316 via a camera switch 318, which is also part of the electronic box 286.

Referring to FIG. 18A, each of stepper motors 278, 290 and 306 on board scanners 14a-14c and tractor 12 is limited in its operation by respective pairs of limit switches (limit switches 308 for the scanner and drive motors or limit switches 310 for the magnet motors), which are connected to the microprocessor inside the respective stepper motor. When a limit switch changes state while the associated motor is driving a component to move, the motor stops rotating (but can still rotate in the opposite direction). The limit switches may be powered by the motor connection.

Referring to FIG. 18B, the system further comprises a multi-segment tower light unit 320 that is used to indicate the state of the system. Light unit 320 receives power from a 24-volt DC power supply 322 via a respective power line in response to activation of switches 324 that are part of relay board 298. Switches 324 are activated by computer 288 via serial (RS-422 or RS-232) port interface 292.

Referring again to FIG. 18A, each of scanners 14a-14d further comprises an X-position encoder 282 that outputs encoder pulses as the selected scanner travels unit distances in the X-direction during scanning. These X-position encoder pulses are received via respective electrical connections by an X-position encoder selector 338 (see FIG. 18B) disposed within electronic box 286. The X-position encoder pulses are then split by an encoder pulse splitter 340. The split pulses are respectively output to a data acquisition device 332 designed to record data from incremental encoders and to a pair of ultrasonic pulser/receivers 334a and 334b. (In accordance with one implementation, the data acquisition device may be a USB4 encoder data acquisition USB device commercially available from US Digital, Vancouver, Wash.) The data acquisition device 332 in turn sends the X-position data to the motion control software application that runs on the computer 288. The ultrasonic pulser/receivers 334a,b send the X-position data to the NDI scan software application that runs on the computer.

Referring to FIG. 18A, each of radius scanners 14b and 14c further comprises a scanner Y-position encoder 336 that outputs encoder pulses as the sweeping radius array 280a or 280b of the selected radius scanner rotates unit angles during radius scanning. (The spar strip scanner 14d does not scan in the Y-direction, so it does not include a Y-position encoder. The spar arm scanner 14a shown in FIG. 18A also does not incorporate a Y-position encoder, but as will be explained later, it does provide information to enable simulated Y-position encoder pulses to be generated.) The Y-position encoder pulses from radius scanners 14b,c are received via by a Y-position encoder selector 284 (see FIG. 18B) disposed within electronic box 286. The Y-position encoder pulses are then split by an encoder pulse splitter 330. Again the split pulses are respectively output to data acquisition device 332 and to ultrasonic pulser/receivers 334a,b. The data acquisition device 332 in turn sends the Y-position data to the motion control software application that runs on the computer 288. The ultrasonic pulser/receivers 334a,b send the Y-position data to the NDI scan software application that runs on the computer.

In accordance with the specific implementation shown in FIG. 18, the various X- and Y-position encoders may receive power from a 5-volt DC power supply 312 via a respective power line in response to activation of a switch 314 that is part of relay board 298. The respective power lines from switch 314 to the position encoders are not shown in FIG. 18 to avoid clutter. Switch 314 is activated by computer 288 via serial (RS-422 or RS-232) port interface 292.

In the instances where the spar arm scanner is being used, horizontal and vertical position data describing the location of the sensor head relative to a starting point on the horizontal stabilizer are needed by the scan application in order to correctly align the data coming from the elements of the NDI sensor. This data is provided to the scan application in terms of encoder pulses (with quadrature or direction information). In the present system arrangement, a wheel rotation encoder measures the horizontal position of the spar arm scanner and is sent directly to the scan application, but the vertical measurement (as described above) is more complex due to the non-linear kinematics of the arm motion (previously explained with reference to FIG. 10) and requires a different type of implementation.

As described earlier, the kinematic equations of motion for the spar arm scanner provide the relationship between the rotation of the scanner motor 278 (i.e., the same as lead screw motor 46 in FIG. 9A) and the height of the web array 348. From this relationship the number of pulses (which is proportional to the number of motor rotations) can be computed. In the implementation depicted in FIG. 18, the control computer 288 instructs the spar arm scanner motor 278 that drives the lead screw to rotate a specific number of steps and then sends the scanner motor 278 a command to send back the internal encoder position. This option does not use the internal motor encoder data directly; instead the computer 288 requests a single position with an API command (through serial interface 292). This is because the particular stepper motor used does not output the raw internal encoder data directly. In other embodiments where a stepper motor with an internal encoder that can output raw encoder pulses is used, then the encoder output could be utilized for continuously updated arm height measurement.

For the spar arm scanner, the arm height value is computed by the motion control software kinematics equations and then the data acquisition device 332 is instructed by the motion control software to generate the corresponding quadrature pulses. These simulated encoder pulses are sent to the ultrasonic pulser/receivers 334a,b. The ultrasonic pulser/receivers also receive pulses generated by the X-axis encoder 282 (see FIG. 18A) via a switch 338 and splitter 340 (see FIG. 18B). The pulser/receivers send the encoder pulses to the NDI scan software. The NDI scanning software application interprets the simulated encoder pulses as a height value, which is used (along with the X-encoder values) to position the scan data in the proper location.

The motion control application software running on computer 288 (see FIG. 18B) also controls the radius scanner motor 278 (see FIG. 18A) to produce specified sweeping motions of a sweeper bridge assembly (see FIGS. 10-12 in U.S. patent application Ser. No. 13/466,285) of the radius scanner that is loaded. The sweep angle of the sweeper bridge in both directions is limited by limit switches 308 at the extents of the motion range on radius scanners 14b and 14c, the sweep angle can also be controlled programmatically. A Y-axis encoder 336 measures the angular position of the shaft of the radius scanner motor 278, which in turn determines the angular position of the sweeper bridge assembly. The sweeping motion of the bridge assembly is synchronized with the motion of the radius scanner platform in the X-direction, the position of the radius scanner platform in the X-direction being indicated by X-axis encoder 282. The motion control application receives encoded data from both encoders 282 and 336.

Cable Management System

Figure 19:
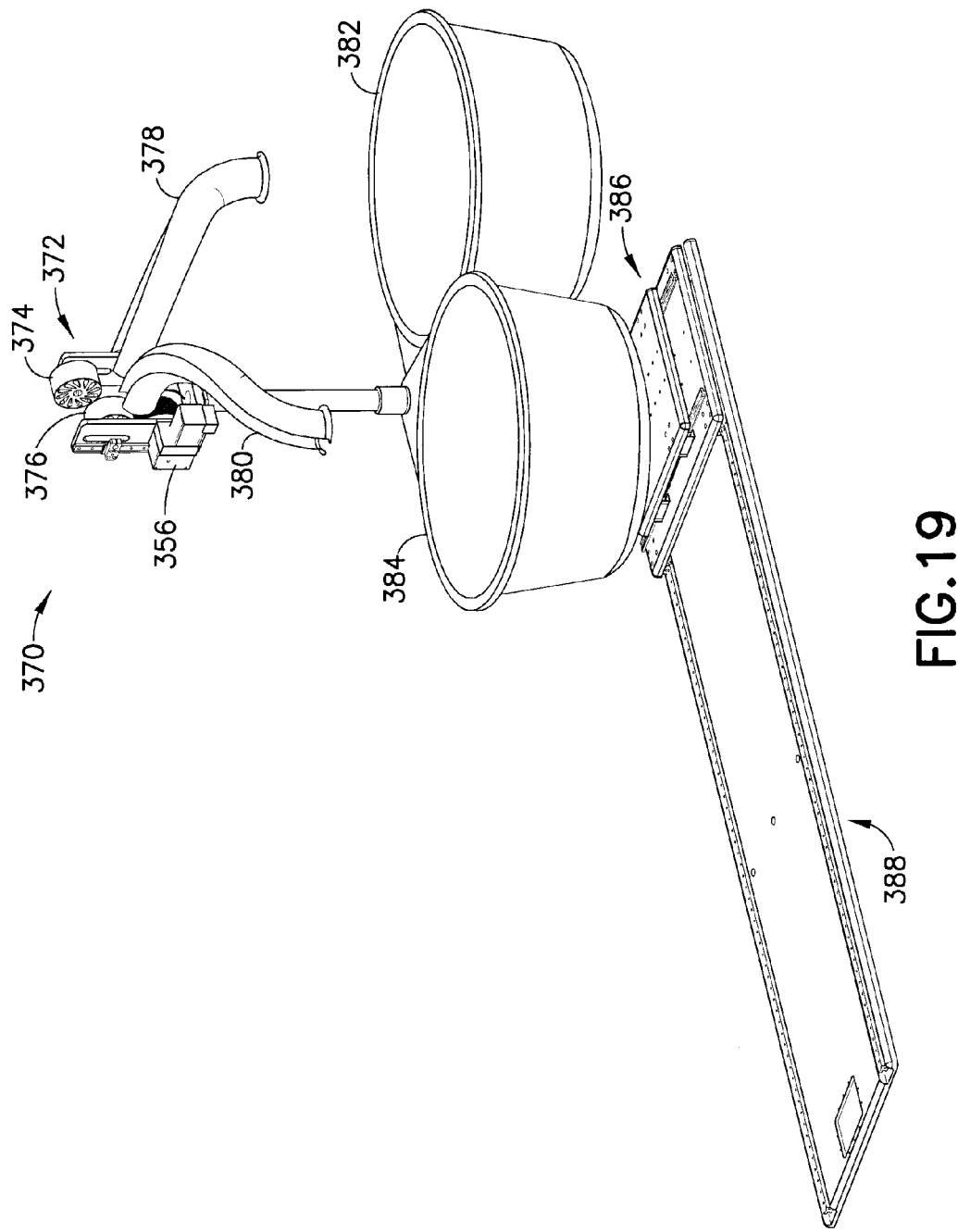
FIG. 19 is a diagram showing an isometric view of a cable management system in accordance with one embodiment.

Still referring to FIG. 18B, the motion control application software running on computer 288 also controls a cable motor 356 of a cable management system 370. When each of the scanners is operated, respective tractor and scanner cables need to accompany the scanner and the tractor down the length of the horizontal stabilizer. Referring to FIG. 19, the cable management system 370 comprises a cable drive system 372, a pair of buckets 382 and 384 which hold wound portions of the tractor and scanner cables respectively, and a platform 386 which rides on rails of a rotatable base 388. The cable drive system 372 comprises two pairs of opposing wheels (only wheels 374 and 376 are visible in FIG. 19) that grip the cables (not shown) and are driven to rotate by cable motor 356 under computer control. The motion control software running on computer 288 synchronizes the movement of the cables with the movement of the active trailer and the tractor, extending or retracting the cables as appropriate. The computer system is programmed to control the cable motor in dependence on scanner X-position information derived from pulses generated by the X-position encoder of the scanner connected to the scanner cable.

One side of the cable drive system is occupied by the tractor cable. The other side of the cable drive system is occupied by a scanner cable bundle. Each scanner has a cable bundle that provides air, water, electrical power and electronic data. Each scanner cable is swapped out when scanners are changed. Respective portions of the cable from the tractor are gripped by the first pair of wheels, guided by a first cable guide 378 and held in a first bucket 382 hung from a post on which the cable drive system is mounted. Similarly, respective portions of the cable from the loaded scanner are gripped by the second pair of wheels, guided by a second cable guide 380 and held in a second bucket 384 hung from the post. Bucket 384 sits on a set of sliding platforms that allow X/Y motion of the bucket as the cable is extended or retracted. The entire base 388 is rotatable about an axis located at the middle circle of the row of three circles. Each cable guide is channel-shaped and open along its entire length to allow removal of the cable therein. When scanners are changed, the cable of the unloaded scanner is removed from the cable drive system 372 and cable guide 380, and bucket 384 is unloaded with the unloaded scanner, and a different bucket holding portions of the cable of the newly loaded scanner is hung on the post, with other portions of the latter cable being placed inside cable guide 380 and passed through the cable drive system.

In addition to NDI-specific types of inspection, other types of inspection or manufacturing applications may be able to take advantage of the mechanical and control concepts presented here. For example, the NDI sensor carried by the payload platform can be replaced by other components, such as: laser scanners, video cameras, robotic manipulators, reflective targets, paint heads, or other electro-mechanical components.

While various embodiments have been described, it will be understood by those skilled in the art that various changes may be made and equivalents may be substituted for elements thereof without departing from the scope of the teachings herein. In addition, many modifications may be made to adapt a particular situation to the teachings herein without departing from the scope thereof. Therefore it is intended that scope of the claims set forth hereinafter not be limited to the disclosed embodiments.

As used in the claims, the term "computer system" should be construed broadly to encompass a system having at least one computer or processor, and which may have two or more interconnected computers or processors.

Furthermore, the method claims set forth hereinafter should not be construed to require that the steps recited therein be performed in alphabetical order or in the order in which they are recited.

The invention claimed is:

1. A method for scanning spars of a hollow structure containing spars, each spar comprising first and second filleted join regions connected by a web, said method comprising:
   (a) moving a first sensor along the first filleted join region;
   (b) actuating the first sensor to transmit beams into the first filleted join region during step (a);
   (c) moving a second sensor along a first strip-shaped area of the web adjacent to the first filleted join region;
   (d) actuating the second sensor to transmit beams into the first strip-shaped area during step (c);
   (e) moving a third sensor along a second strip-shaped area of the web that is not adjacent to the first filleted join region; and
   (f) actuating the third sensor to transmit beams into the second strip-shaped area during step (e).

2. The method as recited in claim 1, further comprising:
   (g) moving the third sensor along a third strip-shaped area of the web that is not adjacent to the first filleted join region and is partially overlapping with the second strip-shaped area; and
   (h) actuating the third sensor to transmit beams into the third strip-shaped area during step (g).

3. The method as recited in claim 1, further comprising:
   (g) moving a fourth sensor along the second filleted join region; and
   (h) actuating the fourth sensor to transmit beams into the second filleted join region during step (g).

4. The method as recited in claim 1, further comprising:
   (g) moving the second sensor along a second strip-shaped area of the web adjacent to the second filleted join region;
   (h) actuating the second sensor to transmit beams into the second strip-shaped area during step (g).

5. The method as recited in claim 1, wherein the beams transmitted by each of the first, second and third sensors are ultrasound beams, further comprising:
   supplying acoustic couplant between the first sensor and the first filleted join region during step (b);
   supplying acoustic couplant between the second sensor and the first strip-shaped area during step (d); and
   supplying acoustic couplant between the third sensor and the second strip-shaped area during step (f).

6. The method as recited in claim 1, further comprising sweeping the first sensor back and forth across the first filleted join region during step (a).

7. The method as recited in claim 1, further comprising:
   (g) placing a first scanner carrying the first sensor inside a tunnel adjacent the spar being inspected prior to step (a);
   (h) removing the first scanner from the tunnel after step (b);
   (i) placing a second scanner carrying the second sensor inside the tunnel prior to step (c);
   (j) removing the second scanner from the tunnel after step (d);
   (k) placing a third scanner carrying the third sensor inside the tunnel prior to step (e); and
   (l) removing the third scanner from the tunnel after step (f).

8. The method as recited in claim 7, wherein:
   step (g) comprises magnetically coupling the first scanner to a motorized vehicle disposed outside the hollow structure;
   step (a) comprises actuating the motorized vehicle to pull the first scanner; and step (h) comprises uncoupling the first scanner from the motorized vehicle.

9. The method as recited in claim 8, wherein:
step (i) comprises magnetically coupling the second scanner to the motorized vehicle disposed outside the hollow structure;
step (c) comprises actuating the motorized vehicle to pull the second scanner; and
step (j) comprises uncoupling the second scanner from the motorized vehicle.

10. The method as recited in claim 1, wherein steps (a) through (f) are performed for each of first and second spars of the hollow structure, further comprising:
placing the hollow structure on first and second support tools which are configurable before any of steps (a) through (f) are performed; and
changing the configuration of the first support tool from a first configuration to a second configuration after steps (a) through (f) have been performed for the first spar and before any of steps (a) through (f) are performed for the second spar.

11. The method as recited in claim 10, further comprising:
placing a first scanner carrying the first sensor inside the tunnel adjacent to the first spar and on top of a bottom skin of the hollow structure prior to performing step (a) for the first spar;
magnetically coupling a motorized vehicle to the first scanner through the bottom skin of the hollow structure prior to performing step (a) for the first spar;
uncoupling the first scanner from the motorized vehicle after steps (a) and (b) have been performed for the first spar;
placing the first scanner carrying the first sensor inside the tunnel adjacent to the second spar and on top of a bottom skin of the hollow structure prior to performing step (a) for the second spar;
magnetically coupling the motorized vehicle to the first scanner through the bottom skin of the hollow structure prior to performing step (a) for the second spar; and
uncoupling the first scanner from the motorized vehicle after steps (a) and (b) have been performed for the second spar,
wherein the first support tool in said first configuration provides clearance for the motorized vehicle when the first scanner is adjacent to the first spar and in said second configuration provides clearance for the motorized vehicle when the first scanner is adjacent to the second spar.

12. The method as recited in claim 1, wherein the hollow structure is a horizontal stabilizer for an aircraft.

13. The method as recited in claim 1, further comprising the following steps performed prior to step (a):
placing a first scanner carrying the first sensor inside a tunnel adjacent the spar being inspected;
graphically depicting an end view of the hollow structure on a display monitor, which graphical depiction depicts a plurality of spaced spars;
graphically depicting an interaction region inside the graphical depiction of the hollow structure on the display monitor, the position of the interaction region relative to the graphical depiction of the hollow structure indicating the position of the first scanner relative to the spar being inspected; and
selecting (e.g. clicking) on the interaction region,
wherein steps (a) and (b) are performed in response to said clicking on the interaction region.

14. A motion control system comprising:
a first scanner that is movable along any one of a first plurality of motion paths within a hollow structure;
a first plurality of motion script files containing sequences of motion commands and parameters respectively associated with said first plurality of motion paths;
a graphical user interface comprising a first window, said first window comprising a row of tabs that access custom control windows for individual scanner devices, a graphical depiction of one end of the hollow structure and a first plurality of interaction regions inside the graphical depiction of the one end of the hollow structure, the position of each interaction region of said first plurality of interaction regions relative to the graphical depiction of the hollow structure indicating the respective position of the first scanner relative to the hollow structure for a respective motion path of said first plurality of motion paths; and
a computer system programmed to execute the sequences of commands in a motion script file corresponding to a selected one of said first plurality of interaction regions, thereby causing said first scanner to move along the corresponding motion path in accordance with its associated parameters.

15. The motion control system as recited in claim 14, further comprising a second scanner that is movable along any one of a second plurality of motion paths within the hollow structure, and
a second plurality of motion script files containing sequences of commands and parameters respectively associated with said second plurality of motion paths, wherein:
said graphical user interface comprises a second window, said second window comprising a row of tabs that access custom control windows for individual scanner devices, a graphical depiction of one end of the hollow structure and a second plurality of interaction regions inside the graphical depiction of the one end of the hollow structure, the position of each interaction region of said second plurality of interaction regions relative to the graphical depiction of the hollow structure indicating the respective position of the second scanner relative to the hollow structure for a respective motion path of said second plurality of motion paths; and
said computer system is further programmed to execute the sequences of commands in a motion script file corresponding to a selected one of said second plurality of interaction regions, thereby causing said second scanner to move along the corresponding motion path in accordance with its associated parameters.

16. A system comprising:
a tractor comprising a frame, a plurality of wheels rotatably mounted to said frame, a drive motor, and first and second magnets;
a plurality of scanners, each scanner comprising a frame, a plurality of wheels rotatably mounted to said frame, first and second magnets arranged for magnetic coupling with said first and second magnets of said tractor, and an X-position encoder;
an electronics box comprising a serial interface, a power supply, a power control switch electrically coupled to said power supply and to said serial interface, an X-position encoder selector, and a data acquisition device electrically coupled to said X-position encoder selector;
a tractor cable comprising a first electrical conductor connecting said drive motor of said tractor to said power control switch and a first plurality of electrical conductors connecting said drive motor to said serial interface;

a plurality of scanner cables respectively connected to said plurality of scanners, each scanner cable comprising a respective electrical conductor connecting a respective X-position encoder to said X-position encoder selector; and a computer system electrically coupled to said data acquisition device and to said serial interface, wherein said computer is programmed to control the states of said power control switch and said X-position encoder selector via said serial interface, and is further programmed to control said drive motor via said serial interface and said first plurality of electrical conductors of said tractor cable in dependence on scanner X-position information derived by said data acquisition device from pulses generated by one of said X-position encoders.

17. The system as recited in claim 16, wherein one of said plurality of scanners further comprises a sensor and a scanner motor for driving movement of said sensor relative to said frame of said one scanner, and the scanner cable connected to said one scanner comprises a second electrical conductor connecting said scanner motor to said power control switch and a second plurality of electrical conductors connecting said scanner motor to said serial interface, wherein said computer system is further programmed to control said scanner motor via said serial interface and said second plurality of electrical conductors in dependence on scanner X-position information derived by said data acquisition device from pulses generated by said X-position encoder of said one scanner.

18. The system as recited in claim 16, wherein said tractor further comprises a magnet motor for driving displacement of said first magnet relative to said frame of said tractor, wherein said computer system is further programmed to control said magnet motor via said serial interface and a second plurality of electrical conductors in dependence on scanner X-position information derived by said data acquisition device from pulses generated by one of said X-position encoders.

19. The system as recited in claim 16, further comprising a cable management system comprising a first pair of rollers for gripping a portion of said tractor cable, a second pair of rollers for gripping a portion of the scanner cable connected to one of said plurality of scanners, and a cable motor for driving rotation of said first and second pairs of rollers, wherein said computer system is further programmed to control said cable motor in dependence on scanner X-position information derived by said data acquisition device from pulses generated by the X-position encoder of said one scanner.

20. The system as recited in claim 16, wherein each of said plurality of scanners comprises a respective chamber for receiving water, further comprising:

a water supply system comprising a plurality of ports and a plurality of water control valves respective disposed between said plurality of ports and a source of water; and a plurality of water lines respectively at least partially incorporated in said plurality of scanner cables, each of said water lines connecting a respective port of said water supply system to a respective one of said chambers of said plurality of scanners, wherein said computer system is further programmed to control the supply of water to said plurality of water control valves so that the currently open water control valve will supply water.

* * * * *